US012703930B2

(12) United States Patent
Sgourakis et al.

(10) Patent No.: US 12,703,930 B2
(45) Date of Patent: Aug. 11, 2026

(54) SYSTEMS AND METHODS FOR IDENTIFICATION OF MHC-I PEPTIDE EPITOPES

(71) Applicant: THE REGENTS OF THE UNIVERSITY OF CALIFORNIA, Oakland, CA (US)

(72) Inventors: Nikolaos G. Sgourakis, Philadelphia, PA (US); Giora Morozov, Santa Cruz, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 903 days.

(21) Appl. No.: 17/790,711

(22) PCT Filed: Jan. 4, 2021

(86) PCT No.: PCT/US2021/012117
§ 371 (c)(1),
(2) Date: Jul. 1, 2022

(87) PCT Pub. No.: WO2021/138688
PCT Pub. Date: Jul. 8, 2021

(65) Prior Publication Data

US 2023/0059548 A1 Feb. 23, 2023

Related U.S. Application Data

(60) Provisional application No. 62/957,040, filed on Jan. 3, 2020.

(51) Int. Cl.
*C40B 30/04* (2006.01)
*C12N 15/10* (2006.01)

(52) U.S. Cl.
CPC .......... *C40B 30/04* (2013.01); *C12N 15/1037* (2013.01)

(58) Field of Classification Search
None
See application file for complete search history.

(56) References Cited

U.S. PATENT DOCUMENTS

| | | | |
|---|---|---|---|
| 11,814,420 | B2 | 11/2023 | Sgourakis |
| 2013/0017213 | A1 | 1/2013 | Liu et al. |
| 2013/0171668 | A1 | 7/2013 | Loset |
| 2014/0127251 | A1 | 5/2014 | Maeurer |
| 2014/0186850 | A1 | 7/2014 | Berniac et al. |
| 2018/0180601 | A1 | 6/2018 | Pedersen et al. |
| 2018/0319870 | A1 | 11/2018 | Amin |

(Continued)

FOREIGN PATENT DOCUMENTS

| | | | |
|---|---|---|---|
| EP | 2127664 | A1 | 12/2009 |
| WO | WO 2020/010261 | | 7/2019 |

(Continued)

OTHER PUBLICATIONS

International Search Report and Written Opinion for related PCT Application No. PCT/US2019/040616—9 pages (Nov. 18, 2019).

(Continued)

*Primary Examiner* — Christian C Boesen
(74) *Attorney, Agent, or Firm* — Morgan, Lewis & Bockius LLP

(57) ABSTRACT

Provided herein are novels systems and methods for the identification of peptides that bind to MHC-I molecules using peptide receptive MHC-I complexes.

20 Claims, 10 Drawing Sheets

Specification includes a Sequence Listing.

(56) References Cited

U.S. PATENT DOCUMENTS

| | | | |
|---|---|---|---|
| 2020/0024654 | A1 | 1/2020 | Heron et al. |
| 2021/0155670 | A1 | 5/2021 | Sgourakis et al. |
| 2021/0269503 | A1 | 9/2021 | Sgourakis |
| 2021/0371498 | A1 | 12/2021 | Sgourakis |
| 2021/0371499 | A1 | 12/2021 | Sgourakis |
| 2022/0042008 | A1 | 2/2022 | Kleinman |
| 2023/0059548 | A1 | 2/2023 | Sgourakis |

FOREIGN PATENT DOCUMENTS

| | | |
|---|---|---|
| WO | WO 2019/145509 | 8/2019 |
| WO | WO 2021/050792 | 3/2021 |
| WO | WO 2021/138685 | 7/2021 |
| WO | WO 2021/138688 | 7/2021 |
| WO | WO 2021/212085 | 10/2021 |

OTHER PUBLICATIONS

European Search Report for related EP Patent Application No. EP 19831548—2 pages (Apr. 11, 2022).

International Search Report and Written Opinion for related PCT Application No. PCT/US20/50276—23 pages (Mar. 15, 2021).

International Search Report and Written Opinion for corresponding PCT Application No. PCT/US21/12117—17 pages (May 21, 2021).

International Search Report and Written Opinion for related PCT Application No. PCT/US21/27841—15 pages (Oct. 1, 2021).

International Search Report and Written Opinion for related PCT Application No. PCT/US21/12114—17 pages (May 20, 2021).

Dash et al., "Quantifiable predictive features define epitope-specific T cell receptor repertoires." Nature 547(7661):89-93 (2017).

Stoeckius et al., "Simultaneous epitope and transcriptome measurement in single cells." Nat Methods (9):865-868 (2017).

Takahashi et al., "An immunodominant epitope of the human immunodeficiency virus envelope glycoprotein gp160 recognized by class I major histocompatibility complex molecule-restricted murine cytotoxic T lymphocytes." Proc Natl Acad Sci USA 85(9):3105-9 (1998).

Kawakami et al., "Identification of the immunodominant peptides of the MART-1 human melanoma antigen recognized by the majority of HLA-A2-restricted tumor infiltrating lymphocytes." J Exp Med. 180(1):347-52 (1994).

Natarajan et al., "An allosteric site in the T-cell receptor Cβ domain plays a critical signalling role." Nat Commun. 8:15260 (2017).

Glanville et al., "Identifying specificity groups in the T cell receptor repertoire." Nature 547: 94-98 (2017).

Bakker et al., "Conditional MHC class I ligands and peptide exchange technology for the human MHC gene products HLA-A1, -A3, -A11, and -B7." Proc. Natl. Acad. Sci. U. S. A. 105: 3825-3830 (2008).

Saini et al., "Dipeptides catalyze rapid peptide exchange on MHC class I molecules." Proc. Natl. Acad. Sci. U. S. A. 112: 202-207 (2015).

Morozov et al., "Interaction of TAPBPR, a tapasin homolog, with MHC-I molecules promotes peptide editing." Proc. Natl. Acad. Sci. U. S. A. 113: E1006-1015 (2016).

Jiang et al., "Crystal structure of a TAPBPR-MHC I complex reveals the mechanism of peptide editing in antigen presentation." Science 358: 1064-1068 (2017).

Jiang et al., "Crystal structure of a TAPBPR-MHC I complex reveals the mechanism of peptide editing in antigen presentation." Science 358: Supplemental Material (2017).

Mcshan et al., "Peptide exchange on MHC-I by TAPBPR is driven by a negative allostery release cycle." Nat. Chem. Biol. 14: 811-820 (2018).

Khan et al., "The structure and stability of an HLA-A*0201/octameric tax peptide complex with an empty conserved peptide-N-terminal binding site." J. Immunol. 164: 6398-6405 (2000).

Garboczi et al., "HLA-A2-peptide complexes: refolding and crystallization of molecules expressed in *Escherichia coli* and complexed with single antigenic peptides." Proc. Natl. Acad. Sci. 89: 3429-3433 (1992).

Johnson et al., "Gene transfer of tumor-reactive TCR confers both high avidity and tumor reactivity to nonreactive peripheral blood mononuclear cells and tumor-infiltrating lymphocytes." J. Immunol. Baltim. Md 1950 177: 6548-6559 (2006).

Hermann et al., "The binding of TAPBPR and Tapasin to MHC class I is mutually exclusive." J. Immunol 191: 5743-5750 (2013).

Trautman et al., "Dominant TCR V alpha usage by virus and tumor-reactive T cells with wide affinity ranges for their specific antigens." Euro J Immunol. 32: 3181-3190 (2002).

Jurtz et al., "NetMHCpan-4.0: Improved Peptide-MHC Class I Interaction Predictions Integrating Eluted Ligand and Peptide Binding Affinity Data." J. Immunol. Baltim. Md 1950 199: 3360-3368 (2017).

Li et al., "Three-dimensional structure of H-2Dd complexed with an immunodominant peptide from human immunodeficiency virus envelope glycoprotein 120." J. Mol. Biol. 283: 179-191 (1998).

Praest et al., "New insights into the structure of the MHC class I peptide-loading complex and mechanisms of TAP inhibition by viral immune evasion proteins." Mol. Immunol., Pergamon, GB, 113 (2018).

Overall et al., "High Throughput pMHC-1 Tetramer Library Production Using Chaperone Mediated Peptide Exchange." bioRxiv, pp. 1-31 (2019).

Overall et al., "High throughput pMHC-1 tetramer library production using chaperone-mediated peptide exchange." Nature Communications. 11(1):1909 (2020).

Jurewicz et al., "MHC-I peptide binding activity assessed by exchange after cleavage of peptide covalently linked to β2-microglobulin." Analytical Biochemistry, Amsterdam NL, 584: (2019).

Kotsiou et al., "Dimerization of soluble disulfide trap single-chain major histocompatibility complex class I molecules dependent on peptide binding affinity." Antioxidants and Redox Signaling. 15:3 (2011).

King et al., "Antibody-peptide-MHC fusion conjugates target non-cognate T cells to kill tumour cells." Cancer Immunol. Immunotherapy 62:6 (2013).

Li et al., "Engineering superior DNA vaccines: MHC class I single chain trimers bypass antigen processing and enhance the immune response to low affinity antigens." Vaccine., 28, pp. 1911-1918 (2010).

Hermann et al., "TAPBPR alters MHC class I peptide presentation by functioning as a peptide exchange catalyst." eLIFE. vol. 4, p. 15 (2015).

O'Rourke et al., "Production of soluble pMHC-I molecules in mammalian cells using the molecular chaperone TAPBPR." Protein Engineering Design. 32:12 (2019).

Lumistra et al., "A flexible MHC class I multimer loading system for large-scale detection of antigen-specific T cells." Journal of Experimental Medicine. 215:5, 1493-1504 (2018).

Letournour et al., "Derivation of a T cell hybridoma variant deprived of functional T cell receptor alpha and beta chain transcripts reveals a nonfunctional alpha-mRNA of BW5147 origin." Eur J Immunol. 19(12):2269-74 (1989).

Ohashi et al., "Reconstitution of an active surface T3/T-cell antigen receptor by DNA transfer." Nature 316(6029):606-9 (1985).

Altman et al., "Phenotypic analysis of antigen-specific T lymphocytes." Science 274(5284):94-6 (1996).

Arstila et al., "A direct estimate of the human alphabeta T cell receptor diversity." Science 286: 958 (1999).

Thomas & Tampé, "Structure of the TAPBPR-MHC I complex defines the mechanism of peptide loading and editing." Science 358: 1060-1064 (2017).

Moritz et al., "High-throughput peptide-MHC complex generation and kinetic screenings of TCRs with peptide-receptive HLA-A*02:01 molecules." Science Immunology. 4:37 (2019).

Saini et al., "Empty peptide-receptive MHC class I molecules for efficient detection of antigen-specific T cells." Science Immunology. 4:37 (2019).

(56) References Cited

OTHER PUBLICATIONS

Nerli et al., "Structure-Based Modeling of SARS-CoV-2 Peptide/HLA-A02 Antigens." Frontiers in Medical Technology. vol. 2 (2020).

Neveu et al., "Impact of CD8-MHC class I interaction in detection and sorting efficiencies of antigen-specific T cells using MHC class I/peptide multimers: contribution of pMHC valency." International Immunology. vol. 18, No. 7, pp. 1139-1145 (2006).

Hansen et al., "Preparation of Stable Single-Chain Trimers Engineered with Peptide, β2 Microglobulin, and MHC Heavy Chain." Current Protocols in Immunology, 17.5.1-17.5.17, (2009).

Science Direct Topics, "Chaperone—An overview." Science Direct https://www.sciencedirect.com/topics/neuroscience/chaperone (2007) Definition which they reside and function, 9 pages (downloaded 2024).

Anjanappa et al., "Structures of peptide-free and partially loaded MHC class I molecules reveal mechanisms of peptide selection." Nature Comm. pp. 1-11 (2020).

HLA Nomenclature, "Hla Allele Numbers 2023" (2 pgs.) (2023).

Jantz-Naeem and Springer, "Venus flytrap or pas de trois? The dynamics of MHC class I molecules." Current Opinion in Immunology, 70: 82-89 (2021).

Kalergis et al., "A simplified procedure for the preparation of MHC/peptide tetramers: chemical biotinylation of an unpaired cysteine engineered at the C-terminus of MHC-I." Journal of Immunological Methods 234 pp. 61-70 (2000).

Hafstrand et al., "Successive crystal structure snapshots suggest the basis for M HC class I peptide loading and editing by tapasin." PNAS vol. 116, No. 11, pp. 5055-5060 (2019).

Saini et al., "Dipeptides promote folding and peptide binding of MHC class I molecules." PNAS vol. 110, No. 38, pp. 15383-15388 (2013).

Ostermeir et al., "Coupling between side chain interactions and binding pocket flexibility in HLA-8*44:02 molecules investigated by molecular dynamics simulations." Molecular Immunology, 63:312-319 (2015).

Preparation of empty, peptide-receptive MHC-I/TAPBPR complexes on a column system for peptide capture

TAPBPR catalyses efficient peptide exchange up to 1:1000 molar ratio with MHC-I (native gel experiment)

| TAPBPR (µg) | 5 | 0 | 0 | 0 | 0.005 | 0.05 | 0.5 | 5 |
|---|---|---|---|---|---|---|---|---|
| gTAX/A2 (5 µg) | - | + | + | + | + | + | + | + |
| Peptide / Charge | - | - | NS | -2 | -2 | -2 | -2 | -2 |

*NS: non-specific peptide

** all loading reactions were incubated overnight with 10-fold molar excess of peptide

Different net charge of MHC-I peptides allows peptide exchange by TAPBPR in native gel experiment

FIG. 7B
FIG. 7C
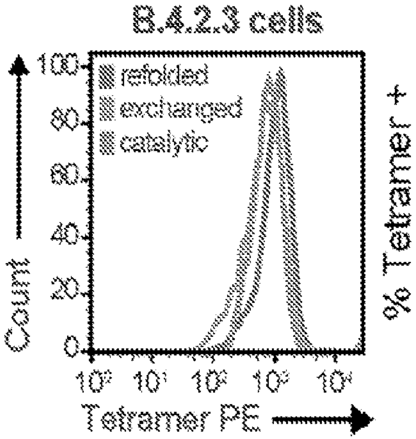
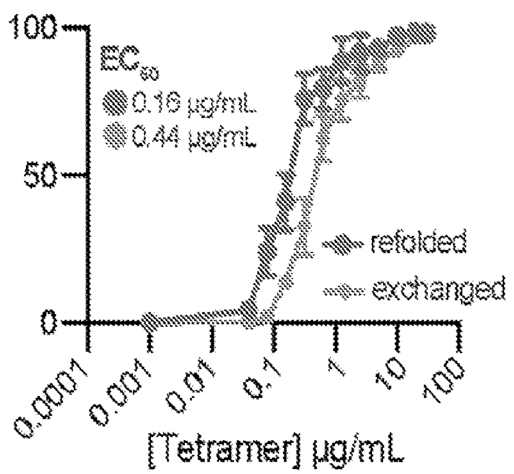
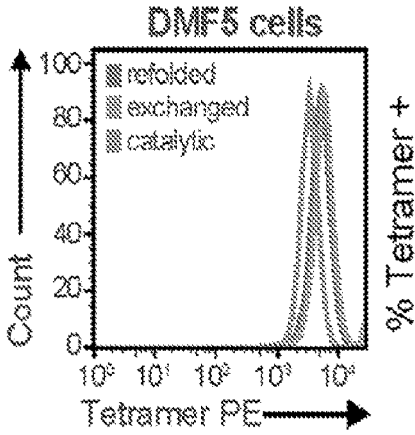
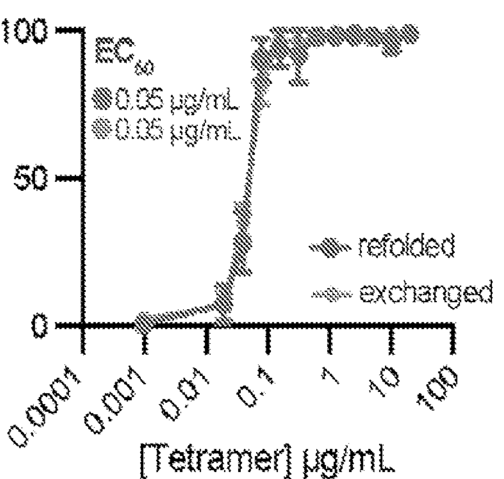
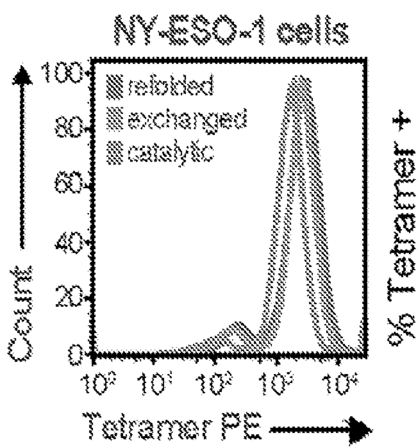
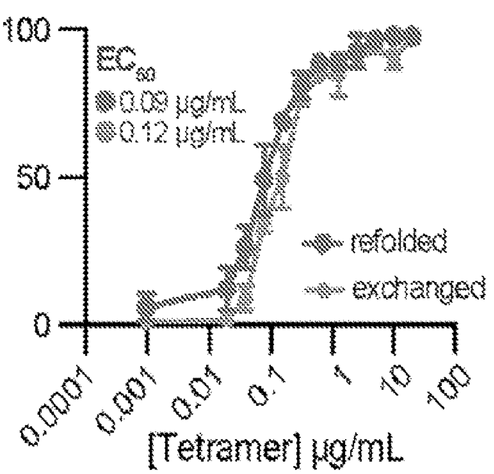

SYSTEMS AND METHODS FOR IDENTIFICATION OF MHC-I PEPTIDE EPITOPES

CROSS REFERENCE TO RELATED APPLICATIONS

The present disclosure claims priority to U.S. Provisional Patent Application No. 62/957,040, filed on Jan. 3, 2020, which is hereby incorporated by reference in its entirety.

STATEMENT OF SUPPORT

This invention was made with government support under Grant Nos. R01AI143997 and R35GM125034 awarded by the National Institutes of Health. The Government has certain rights to this invention.

SEQUENCE LISTING

The present application contains a Sequence Listing which has been submitted electronically in ASCII format and is hereby incorporated by reference in its entirety. Said ASCII copy, created on Jan. 4, 2021, is named 116550-01-5012-WO_ST25.txt and is 9 kilobytes in size.

BACKGROUND

The class-I molecules of the Major Histocompatibility Complex (MHC) play a pivotal role in orchestrating an adaptive immune response by alerting the immune system to the presence of developing infections and tumors. Immune surveillance is achieved through the display of short (8-11 residue long) peptides derived from viral proteins or mutated oncogenes via a tight interaction with the MHC-I peptide-binding groove. Such peptide/MHC-I protein complexes are assembled inside the cell and displayed on the surface of all antigen-presenting cells where the complexes can interact with specialized receptors on T cells and natural killer (NK) cells. The MHC-I proteins are extremely polymorphic (more than 13,000 different alleles have been identified in the human population to date), and each allele can display an estimated 1,000-10,000 different peptides, which makes challenging the prediction of which peptides derived from a protein are presented on MHC-I.

The current state-of-the-art methods for the identification of antigenic peptides that bind to an MHC-I involve liquid chromatography-tandem mass spectrometry (LC/MS/MS). This technique can identify the masses of thousands of peptides extracted from MHC molecules in relevant biological samples. The derived peptide sequences can be cross-referenced with protein sequence databases, and used to train machine learning methods which ultimately predict the specificities of displayed peptides for each MHC allele. See, e.g., Abelin et al., 2017, "Mass Spectrometry Profiling of HLA-Associated Peptidomes in Mono-allelic Cells Enables More Accurate Epitope Prediction," Immunity. February 21; 46(2): 315-326. doi:10.1016/j.immuni.2017.02.007, which is hereby incorporated herein by reference in its entirety. Conventional methods for MHC-I peptidome analysis include acid extraction of peptides (e.g., from the cell surface or from the cell lysate of a biological sample) or the recovery of peptides from purified MHC molecules prior to LC/MS/MS. However, there are significant limitations to these approaches.

Standard acid elution protocols are subject to losses during the peptide purification process, and as a result, it is estimated that up to 80% of relevant peptides are lost in most antigenic peptide identification methods. In addition, a significant number of peptides recovered using standard acid extraction from a cell surface or cell lysate are non-specific for MHC-I. A comparison of peptide repertoires extracted from MHC-I-expressing and β2-microglobulin knockout cells revealed that approximately 50% of the peptides identified as MHC-I peptide ligands are not derived from MHC class I molecules. Analysis is further complicated by the fact that most mammalian cells express multiple (e.g., up to 6) distinct MHC-I alleles, making it difficult to attribute an identified MHC-I peptide ligand to a particular MHC-I allele. Conventional methods might also require the use of tissues and/or cell lines that express high levels of MHC-I, whereas many experimental or clinical samples of interest (e.g., tissues exposed to pathogens and/or tumors) have decreased or downregulated MHC-I expression. Furthermore, transfection of such sample types with exogenous MHC-I is not reliably effective (e.g., for samples with limited starting material and/or low transfection efficiency). See, e.g., Caron et al., "Analysis of Major Histocompatibility Complex (MHC) Immunopeptidomes Using Mass Spectrometry," *Molecular & Cellular Proteomics*, December; 14(12): 2105-3117 doi:10.1074/mcp.O115.052431 (2015), which is hereby incorporated herein by reference in its entirety.

Thus, there remains a need for novel systems and methods for an affinity-based purification process to enable high levels of peptide recovery in an MHC allele-selective manner.

SUMMARY

Provided herein are novels systems and methods for the identification of peptides that bind to MHC-I molecules using peptide receptive MHC-I complexes. Peptide receptive MHC-I complexes are stable for several weeks at 4° C., while their preparation and handling does not require working in dark conditions, as is the case for MHC molecules refolded with photo-cleavable ligands (see, e.g., Bakker et al., Proc. Natl. Acad. Sci. U.S.A., 105:3825-3830 (2008)).

In one aspect, provide, herein is a method of purifying a peptide of interest that binds an WIC class I molecule. This method includes: affixing a peptide receptive MHC-I complex to a solid substrate, the peptide receptive MHC-I complex includes an WIC class I heavy chain and a β2 microglobulin that has been contacted with a molecular chaperone; contacting the peptide receptive MHC-I complex with a plurality of peptides of interest, where at least one of the plurality of peptides of interest binds the peptide-receptive MHC-I complex, resulting in the formation of a peptide-MHC-I complex (pMHC-I); and removing the pMHC-I from the solid substrate, thereby purifying the peptide of interest.

In some embodiments, the method further includes eluting the peptide of interest from the MHC-Class I molecule. In certain embodiments, eluting the peptide of interest includes contacting the pMHC-I with a solution of acidic pH. In certain embodiments, the peptide of interest is eluted in a solution of 10% acetic acid.

In certain embodiments, the method further includes identifying the peptide of interest. In some embodiments, the peptide of interest is identified by a technique including mass spectrometry. In exemplary embodiments, the technique is liquid chromatography-mass spectrometry (LC-MS). In certain embodiments, the technique liquid chromatography-tandem mass spectrometry (LC-MS-MS).

In some embodiments of the method, the peptide-receptive MHC-I complex includes a molecular chaperone. In certain embodiments, the peptide-receptive MHC-I complex is affixed to the solid substrate via an interaction between the molecular chaperone and the solid substrate. In certain embodiments, the molecular chaperone is biotinylated and the solid substrate comprises a biotin binding protein.

In some embodiments, the peptide receptive MHC-I complex is affixed to the solid substrate via an interaction between the MHC class I heavy chain or the β2 microglobulin and the solid substrate. In exemplary embodiments, the MHC Class I heavy chain or the β2 microglobulin is biotinylated and the solid substrate includes a biotin binding protein. In some embodiments, the peptide receptive MHC-I complex includes a molecular chaperone.

In some embodiments, the peptide receptive MHC-I complex was coexpressed with the molecular chaperone in a mammalian cell line. In certain embodiments, the mammalian cell line is a CHO cell line. In some embodiments, the MHC Class I heavy chain is glycosylated. In certain embodiments, the MHC Class I heavy chain is glycosylated at position N86.

In certain embodiments, the peptide receptive MHC-I complex includes a placeholder peptide.

In some embodiments, the method further includes a step of contacting a precursor peptide-MHC-I complex (p*MHC-I) comprising a MHC Class I heavy chain, a β2 microglobulin, and a precursor peptide with the molecular chaperone, thereby forming the peptide receptive MHC-I complex.

In certain embodiments, the molecular chaperone is at a molar excess relative to the p*MHC-I. In some embodiments, the molecular chaperone is at a ratio of more than 1:1, more than 2:1, more than 3:1, more than 4:1, more than 5:1, more than 6:1, more than 7:1, more than 8:1, more than 9:1, or more than 10:1 relative to the p*MHC-I. In some embodiments, the p*MHC-I is at a molar excess relative to the molecular chaperone. In particular embodiments, the molecular chaperone is at a ratio of less than 1:1, less than 1:2, less than 1:5, less than 1:10, less than 1:50, less than 1:100, less than 1:500, or less than 1:1000 relative to the p*MHC-I.

In particular embodiments, the removing the pMHC-I from the solid substrate includes washing with a biotin wash buffer. In some embodiments, the biotin wash buffer includes desthiobiotin. In certain embodiments, the solid substrate includes a bead. In particular embodiments, the bead is a sepharose bead. In some embodiments, the bead is a magnetic bead. In some embodiments, the bead includes a molecular barcode. In certain embodiments, the bead is formed into a column.

In some embodiments, the molecular chaperone is Tapasin Binding Protein Related (TAPBPR).

In certain embodiments, the MHC class I heavy chains are selected from human HLA-A, human HLA-B, human HLA-C, mouse H-2D, or mouse H-2L. In particular embodiments, the MHC class I heavy chain is selected from HLA-A:02, HLA-A:24, or HLA-A:68.

In another aspect, provided herein is a system that includes a peptide receptive MHC-I complexes affixed to a solid substrate, where the peptide receptive MHC-I complex has been contacted with a molecular chaperone. In some embodiments, the peptide receptive MHC-I complex includes a molecular chaperone. In particular embodiments, the peptide receptive MHC-I complex is affixed to the solid substrate via an interaction between the molecular chaperone and the solid substrate.

In certain embodiments of the system, the molecular chaperone is biotinylated and the solid substrate includes a biotin binding protein. In some embodiments, the peptide receptive MHC-I complex is affixed to the solid substrate via an interaction between the MHC class I heavy chain or the β2 microglobulin and the solid substrate. In certain embodiments, the MHC Class I heavy chain or the β2 microglobulin is biotinylated and the solid substrate includes a biotin binding protein.

In some embodiments, the peptide receptive MHC-I complex comprises a molecular chaperone. In certain embodiments, the peptide receptive MHC-I complex was coexpressed with the molecular chaperone in a mammalian cell line. In some embodiments, the mammalian cell line is a CHO cell line. In certain embodiments, the MHC Class I heavy chain is glycosylated. In some embodiments, the MHC Class I heavy chain is glycosylated at position N86.

In certain embodiments, the peptide receptive MHC-I complex comprises a placeholder peptide.

In some embodiments, the solid substrate includes a bead. In certain embodiments, the bead is a sepharose bead. In some embodiments, the bead is a magnetic bead. In certain embodiments, the bead includes a molecular barcode. In certain embodiments, the bead is formed into a column.

In some embodiments of the system, the molecular chaperone is Tapasin Binding Protein Related (TAPBPR).

In certain embodiments, the MHC class I heavy chains are selected from human HLA-A, human HLA-B, human HLA-C, mouse H-2D, or mouse H-2L. In some embodiments, the MHC class I heavy chain is selected from HLA-A:02, HLA-A:24, or HLA-A:68.

In another aspect, provided herein is a kit that includes any of the systems disclosed herein. In some embodiments, the kit further includes an acidic buffer configured to elute a peptide of interest from a pMHC. In some embodiments, the acidic buffer includes 10% acetic acid.

In some embodiments, the kit further includes a wash buffer configured to remove a pMHC from the solid substrate. In some embodiments, the wash buffer is a biotin wash buffer. In certain embodiments, the biotin wash buffer comprises desthiobiotin.

In certain embodiments, the kit includes a peptide of interest. In certain embodiments, the peptide of interest is part of a peptide library. In some embodiments, the peptide library includes at least 10, at least 100, at least $10^3$, at least $10^4$, at least $10^5$, at least $10^6$, at least $10^7$, at least $10^8$, at least $10^9$, or at least $10^{10}$ different peptides of interest.

In another aspect, provided herein is a kit that includes: a placeholder peptide MHC-I complexes (p*MHC-I), where the p*MHC-I includes an MHC class I heavy chain, a β2 microglobulin, and a placeholder peptide; a solid substrate; and a molecular chaperone. In this kit, one or more of the MHC class I heavy chains, β2 microglobulins, or molecular chaperones comprises a binding moiety and where the solid substrate comprises a capture moiety. In some embodiments, the binding moiety is biotin and the capture moiety is a biotin binding protein.

In certain embodiments, the kit includes an acidic buffer configured to elute a peptide of interest from a pMHC-I. In some embodiments, the acidic buffer comprises 10% acetic acid.

In some embodiments, the kit further includes a wash buffer configured to remove a pMHC from the solid substrate. In particular embodiments, the wash buffer is a biotin wash buffer. In exemplary embodiments, the biotin wash buffer includes desthiobiotin.

In some embodiments, a peptide of interest. In certain embodiments, the peptide of interest is part of a peptide library. In some embodiments, the peptide library includes at least 10, at least 100, at least $10^3$, at least $10^4$, at least $10^5$, at least $10^6$, at least $10^7$, at least $10^8$, at least $10^9$, or at least $10^{10}$ different peptides of interest.

In certain embodiments, the solid substrate comprises a bead. In some embodiments, the bead is a sepharose bead. In some embodiments, bead is a magnetic bead. In certain embodiments, the bead includes a molecular barcode. In some embodiments, the bead is formed into a column.

In some embodiments of the kit, the molecular chaperone is Tapasin Binding Protein Related (TAPBPR). In some embodiments, the MHC class I heavy chains are selected from human HLA-A, human HLA-B, human HLA-C, mouse H-2D, or mouse H-2L. In certain embodiments, the MHC class I heavy chain is selected from HLA-A:02, HLA-A:24, or HLA-A:68.

In yet another aspect, provided herein is a kit that includes: a peptide receptive MHC-I complex, where the peptide receptive MHC-I complex comprises an MHC class I heavy chain that is glycosylated in at least one native glycosylation position and a β2 microglobulin; and a solid substrate; where at least one of the MHC class I heavy chain and the β2 microglobulin comprise a binding moiety and where the solid substrate comprises a capture moiety.

In some embodiments, the capture moiety is biotin and the capture moiety is a biotin binding protein.

In some embodiments, the kit further includes an acidic buffer configured to elute a peptide of interest from a pMHC-I. In some embodiments, the acidic buffer includes 10% acetic acid.

In some embodiments, the kit further includes a wash buffer configured to remove a pMHC from the solid substrate. In some embodiments, the wash buffer is a biotin wash buffer. In certain embodiments, the biotin wash buffer comprises desthiobiotin.

In some embodiments, a peptide of interest. In certain embodiments, the peptide of interest is part of a peptide library. In some embodiments, the peptide library includes at least 10, at least 100, at least $10^3$, at least $10^4$, at least $10^5$, at least $10^6$, at least $10^7$, at least $10^8$, at least $10^9$, or at least $10^{10}$ different peptides of interest.

In certain embodiments, the solid substrate comprises a bead. In some embodiments, the bead is a sepharose bead. In some embodiments, bead is a magnetic bead. In certain embodiments, the bead includes a molecular barcode. In some embodiments, the bead is formed into a column.

In some embodiments of the kit, the molecular chaperone is Tapasin Binding Protein Related (TAPBPR). In some embodiments, the MHC class I heavy chains are selected from human HLA-A, human HLA-B, human HLA-C, mouse H-2D, or mouse H-2L.

BRIEF DESCRIPTION OF THE DRAWINGS

The implementations disclosed herein are illustrated by way of example, and not by way of limitation, in the figures of the accompanying drawings. Many modifications and variations of the disclosure can be made without departing from its spirit and scope, as will be apparent to those skilled in the art.

FIGS. 7A, 7B, and 7C illustrate results of proof-of-concept assays for TAPBPR-mediated MHC-I peptide exchange, in accordance with some embodiments. TAPBPR catalyzes efficient peptide exchange when present at up to 1:100 molar ratio with MHC-I.

DETAILED DESCRIPTION

In one aspect, provided herein is a method of isolating a peptide for identification. The method comprises obtaining a plurality of candidate peptide ligands and affixing a peptide receptive complex comprising an MHC class I (MHC-I) molecule (a peptide receptive MHC-I complex) to a solid substrate. The method further comprises contacting the peptide receptive complex with a plurality of peptides of interest, where each respective peptide of interest that binds the MHC-I molecule thereby forming a peptide-MHC-I complex (pMHC-I). The method further comprises releasing the pMHC-I from the solid substrate and recovering the peptide of interest from the peptide receptive MHC-I complex.

Figure 2:
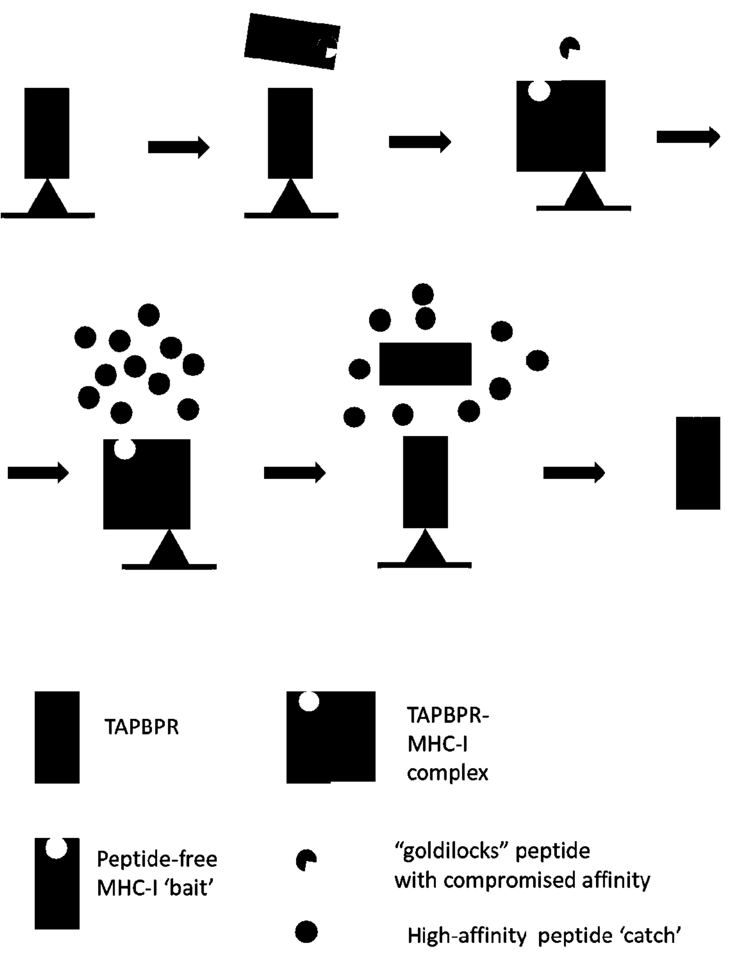
FIG. 2 provides a schematic of a column system for isolating a peptide using empty, peptide-receptive MHC-I/TAPBPR complexes, in accordance with some embodiments.
Figure 3:
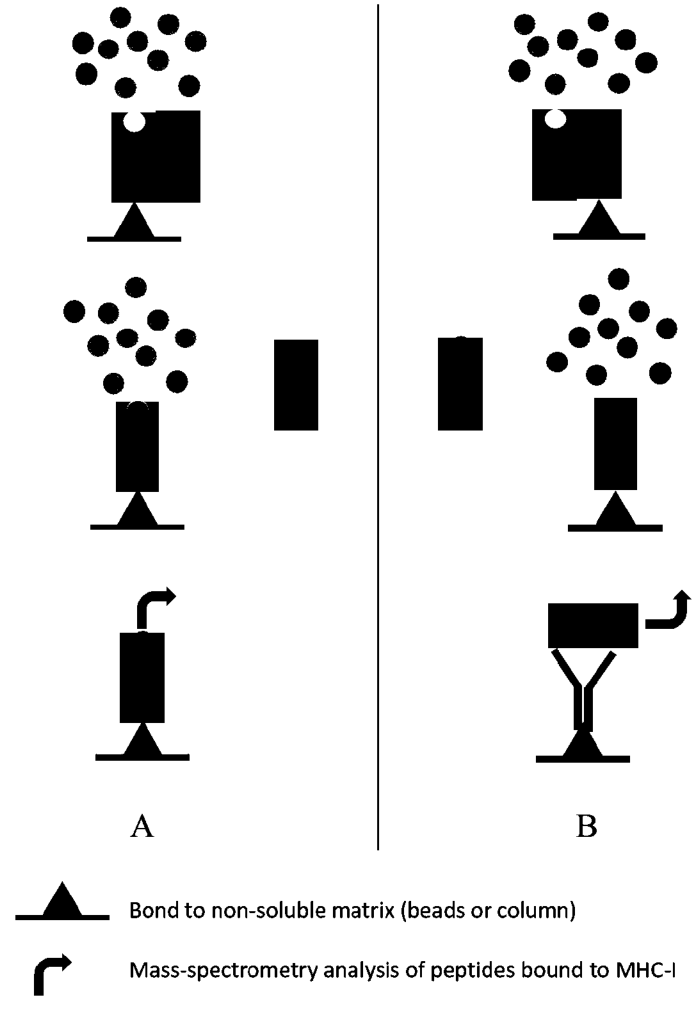
FIGS. 3A and 3B provide schematics of two alternative methods for enrichment of high-affinity peptides using a peptide-receptive MHC-I/TAPBPR complex, in accordance with some embodiments.

A schematic for one aspect of the systems and methods disclosed herein, in accordance with some embodiments, is depicted in FIG. 2. A TAPBPR protein is affixed to a solid surface. It forms a complex with an MHC-I molecule comprising an MHC Class I heavy chain, β2 microglobulin, and a placeholder ("goldilocks") peptide (termed a p*MHC-I herein). As depicted in FIG. 3 and without being bound by theory, the complex formation between TAPBPR and the p*MHC-I results in the loss of the placeholder peptide. The resulting complex is a peptide receptive MHC-I complex. As depicted in FIG. 2 and without being bound by theory, the surface-affixed peptide receptive MHC-I complexes are contacted with a plurality of peptides of interest and the binding of the high affinity peptide of interest to the peptide receptive MHC-I complex removes the pMHC-I from the complex with the TAPBPR. The pMHC-I can be further purified and the peptides disassociated from the pMHC-I.

In other aspects of the systems and methods disclosed herein, a catalytic amount of TAPBPR is used. In such a system, p*MHC-I complexes described above are affixed to a solid surface. The p*MHC-I complexes are then contacted with a TAPBPR. The TAPBPR can be provided in a molar excess relative to the p*MHC-I or the TAPBPR can be provided in a catalytic amount relative to the p*MHC-I. For example in a catalytic amount of TAPBPR, the molar ratio of TAPBPR to p*MHC-I can be less than 1:2, less than 1:5, less than 1:10, less than 1:50, less than 1:100, less than 1:500, or less than 1:1000. The contacting the affixed p*MHC-I with the catalytic amount of TAPBPR produces a peptide receptive MHC-I complex. This complex may (but need not) include a TAPBPR. In some embodiments, the complex includes a placeholder peptide. In other embodiments, the complex does not include a placeholder peptide. Peptides of interest are subsequently introduced to the affixed peptide receptive MHC-I complexes, resulting in a population of affixed pMHC-I complexes. The affixed pMHC-I complexes can be removed from the solid surface and then then purified.

FIG. 3 illustrates aspects of the identification and analysis of peptides of interest that have bound the peptide receptive MHC-I complexes. FIG. 3 Panel A illustrates peptides of interest that include a plurality of peptides that specifically bind to the MHC-I molecule (black circles) and a plurality of peptides that do not bind the peptide receptive MHC-I complex (gray circles). The peptide receptive MHC-I molecule is bound to the solid substrate. As illustrated, a peptide specifically binds to the peptide receptive MHC-I complex, releasing TAPBPR and forming a pMHC-I complex. The pMHC-I complex can be released from the solid substrate and analyzed. In some aspects, the bound peptide is released from the MHC-I and analyzed. In further examples of this aspect, the bound peptide is released from the MHC-I after removal of the MHC-I from the solid substrate. In still further examples, the bound peptide is released from the MHC-I while the MHC-I remains affixed to the solid substrate. In other aspects, the bound peptide is analyzed while still in the pMHC-I complex.

FIG. 3 Panel B illustrates a TAPBPR affixed to the solid substrate in complex with a peptide receptive MHC-I complex. The peptide receptive MHC-I complex is released from the TAPBPR upon binding of a peptide specific for the MHC-I, forming a soluble pMHC-I complex. These soluble pMHC-I complexes can be purified from the supernatant and analyzed. The bound peptide can be released from the MHC-I and analyzed or, alternatively, the bound peptide can be analyzed while still in the pMHC-I complex.

In still further aspects of the systems and methods, a peptide receptive MHC-I complex made by contacting a complex comprising an MHC Class I heavy chain and β2 microglobulin with a molecular chaperone such as TAPBPR is provided. This peptide receptive MHC-I complex is then affixed to the solid substrate. In some aspects of the invention, the peptide receptive MHC-I complex comprises a TAPBPR. In other aspects, the peptide receptive MHC-I complex comprises a placeholder peptide. In still other aspects, the peptide receptive MHC-I complex comprises both a TAPBPR and a placeholder peptide. In still other aspects, the peptide receptive MHC-I complex comprises neither a TAPBPR nor a placeholder peptide. The peptide receptive MHC-I complex can further comprise protein tags or other conjugates that aid in purification, in affixing the peptide receptive MHC-I complex to the solid substrate, and in peptide or MHC-I identification. In aspects such conjugates can include an AviTag that can be specifically biotinylated using BirA, biotin, streptavidin, a DNA barcode, or any of a number of protein tags used for purification, binding, or identification that are well known to one of skill in the art.

In still further aspects of the systems and methods, a peptide receptive MHC-I complex made by coexpressing an MHC Class I heavy chain, β2 microglobulin, and a chaperone such as TAPBPR in a mammalian cell is provided. This peptide receptive MHC-I complex is then affixed to the solid substrate. In some aspects of the invention, the peptide receptive MHC-I complex comprises a TAPBPR. In other aspects, the peptide receptive MHC-I complex comprises a placeholder peptide. In still other aspects, the peptide receptive MHC-I complex comprises both a TAPBPR and a placeholder peptide. In still other aspects, the peptide receptive MHC-I complex comprises neither a TAPBPR nor a placeholder peptide. The peptide receptive MHC-I complex can further comprise protein tags or other conjugates that aid in purification, in affixing the peptide receptive MHC-I complex to the solid substrate, and in peptide or MHC-I identification. In aspects such conjugates can include an AviTag that can be specifically biotinylated using BirA, biotin, streptavidin, a DNA barcode, or any of a number of protein tags used for purification, binding, or identification that are well known to one of skill in the art. In such aspects, the peptide receptive MHC-I is glycosylated. In further examples, the peptide receptive MHC-I is glycosylated at residue N86 (or an equivalent).

A. MI-IC Class I

As used herein, an "MHC class I," "Major Histocompatibility Complex class I," "MHC-I" and the like all refer to a member of one of two primary classes of major histocompatibility complex (MHC) molecules (the other being MHC class II). MHC-I molecules are found on the cell surface of all nucleated cells in the bodies of j awed vertebrates. MHC class I molecules function to display peptide fragments of antigen to other cells of the immune system, including cytotoxic T cells and natural killer (NK) cells. Recognition of an antigenic peptide fragment in the context of an MHC-I by a receptor on the T cell or NK call (such as the T cell receptor) results in an immune response. Typically, the response is the effector cell mediated killing of the cell expressing the antigenic peptide.

MHC-I molecules are heterodimers that include an α-chain (referred to herein as an MHC Class I heavy chain) and a β2-microglobulin (also referred to herein as an MHC class I light chain). The two chains are typically linked via noncovalent interactions between the β2-microglobulin and the α3 domain of the heavy chain and floor of the α1/α2 domain. The heavy chain is polymorphic and encoded by an HLA gene in humans (termed an H-2 gene in mice, RT1 in rats, B in domestic fowl, and LA in other mammals—RhLA, BoLA, etc.). The β2-microglobulin is conserved within a species and encoded by the Beta-2 microglobulin gene. The α3 domain is plasma membrane-spanning and interacts with, for example, the CD8 co-receptor of T cells. For CD8+ cytotoxic T cells to react, the α3-CD8 interaction holds the MHC-I molecule in place while the T cell receptor (TCR) on the surface of the cytotoxic T cell binds its ligand, which is a specific antigenic peptide in the context of the MHC-I. The α1 and α2 domains of the heavy chain fold to make up a groove that accepts peptides. MHC class I molecules bind peptides that, in most cases, are 8-10 amino acids in length.

As described above, MHC class I is termed the "H-2 complex" or "H-2" and include the H-2D, H-2K and H-2L subclasses. In humans, MHC class I molecules include the highly polymorphic human leukocyte antigens HLA-A, HLA-B, HLA-C and the less polymorphic HLA-E, HLA-F, HLA-G, HLA-K and HLA-L. Each human leukocyte antigen (e.g., HLA-A) includes multiple alleles. For example, HLA-A includes over 2,430 non-redundant known alleles.

In some embodiments, the MHC-I constructs provided herein include a single-chain MHC-I. Such single-chain MHC-Is include a MHC-I heavy chain covalently attached to a β2-microglobulin. In some embodiments, the single-chain MHC-I includes, from N- to C-terminus, MHC-I heavy chain-linker-02 microglobulin. In another exemplary embodiment, the single-chain MHC includes, from N- to C-terminus, β2 microglobulin-linker-MHC-I heavy chain. In other embodiments, the MHC-I constructs include an MHC-I where the MHC-I heavy chain and β2 microglobulin are separate and not covalently attached by a linker. In certain embodiments, the MHC-I constructs include a MHC-I heavy chain and a β2-microglobulin that are non-covalently linked to each other.

Any suitable MHC heavy chain can be used in the disclosed methods and systems. In some embodiments, the MHC heavy chain is an HLA-A heavy chain. In other embodiments, the MHC heavy chain is an HLA-B heavy chain. In still other embodiments, the MHC heavy chain is an HLA-C heavy chain. In an exemplary embodiment, the MHC heavy chain is an HLA-A02, HLA-A24, or HLA-A68 heavy chain. In particular embodiments, the MHC-I includes an HLA-A2:01 allele heavy chain, etc. In other embodiments, the MHC-I protein construct includes a mouse H-2. In certain embodiments, the H-2 is an H-2D, H-2K or H-2L. In exemplary embodiments, the H-2 is H-2$D^D$ or H-2$L^D$. In some embodiments, the MHC construct includes a variant of a wild-type MHC-I heavy chain. In particular embodiments, the variant MHC-I heavy chain has at least 80%, 85%, 90%, 91%, 92%, 93%, 94%, 95%, 96%, 97%, 98% or 99% sequence identity to a wild-type MHC-I heavy chain. For embodiments that include a single chain MHC-I molecule, any suitable linker can be used to attach the MHC-I heavy chain to the β2 microglobulin. In certain embodiments, the linker is (GGGS)X, wherein X is 1, 2, 3, 4, 5, 6, 7, 8, 9, 10. In an exemplary embodiment, the linker is (GGGS).

MHC-I molecules can be conjugated to protein and other macromolecule backbones to form multimers that include two or more of the MHC-I molecules (e.g., MHC-I multimers.) In certain embodiments, the multimers include 2, 3, 4, 5, 6, 7, 8, 9 or 10 or more MHC-I molecules. Such macromolecule backbones include streptavidin, which is bound to biotinylated MHC-I molecules to form MHC-I tetramers See, Sims et al., "MHC-peptide tetramers for the analysis of antigen-specific T cells," *Expert Review of Vaccines,* 9:7, 765-774 (2010), which is hereby incorporated herein by reference in its entirety. Other macromolecule backbones include biotinylated coiled coil multimerization domains, which can be conjugated to strepatavidin-MHC-I constructs to form MHC-I pentamers, and dextran, which is bound to 10 or more MHC-I molecules to form MHC-I Dextramers®. See, e.g., Bakker and Schumacher, *Current Opinion in Immunology* 17(4): 428-433 (2005); and Davis et al., *Nature Reviews Immunology* 11:551-558 (2011).All of these macromolecule backbones can be fluorescently or otherwise labeled to aid in the detection of MHC-I-peptide specific T cells.

In some embodiments, the MHC-I molecule includes a protein tag that facilitates multimerization. Some such protein tags can be biotinylated, thereby allowing the attachment of single-chain MHC-I molecules to macromolecule backbones to form multimers. In some embodiments, the protein tag conjugated to the MHC-I molecule includes one or more amino acid residues that are can be biotinylated. In an exemplary embodiment, the protein tag includes exactly one amino acid residue that can be biotinylated. In certain embodiments, the amino acid residue is a lysine residue. In particular embodiments, the protein tag is an AVITAG (GLNDIFEAQKIEWHE) that includes one lysine residue that can be biotinylated by a biotin ligase such as BirA.

Peptide receptive MHC-I complexes (such as those created by interaction of a complex comprising an WIC Class I heavy chain, and a β2 microglobulin with a chaperone such as TAPBPR) can be provided as monomers or multimers. Such peptide receptive MHC-I complexes may (but need not) include a placeholder peptide and may (but need not) be complexed with a chaperone, such as TAPBPR.

Peptide receptive MHC-I complexes can further include one or more purification tags that facilitate purification of the peptide-receptive unit (e.g., of the peptide-receptive unit/chaperone complexes). In some embodiments, the purification tag allows for affinity purification of the peptide-receptive unit/chaperone complexes from cell culture medium. Suitable purification tags that can be included in the MHC-I molecule include, but are not limited to, histidine tags, Strep-tags®, MYC-tags and HA-tags. In an exemplary embodiment, the purification tag is a Strep-tags®. Such purification tags can also be used to affix the peptide receptive MHC-I complex to a solid substrate.

Peptide receptive MHC-I complexes, particularly peptide receptive MHC-I complex multimers can contain conjugates that identify a particular MHC-I allele. Such conjugates include DNA barcodes that allow pooling of multiple MHC-I alleles into a single analysis. In other examples, DNA barcodes are conjugated to the solid substrate (e.g. a bead.) Barcoding of MHC-I molecules is described in, for example, WO2019/157529 (15 Aug. 2019); which is incorporated by reference in its entirety herein, in particular paragraphs [00018] and [00552]-[00595].

In some embodiments, the solid substrate comprises a bead such as a sepharose or other appropriate bead. Such beads can be packed into a column. In other embodiments, the solid substrate comprises a magnetic bead. In some embodiments, the peptide receptive MHC-I complex is affixed to the solid substrate prior to contacting the peptides of interest with the peptide receptive MHC-I complex. In other embodiments, the contacting the peptides of interest with the peptide receptive MHC-I complex occurs prior to the affixing the resulting pMHC-I to the solid substrate (via the MHC-I heavy chain, MHC-I light chain or the molecular chaperone if the molecular chaperone is provided in a stoichiometric amount). In still other embodiments, a p*MHC-I is affixed to the solid substrate, contacted with a stoichiometric or catalytic amount of the molecular chaperone (e.g., TAPBPR), thereby forming a peptide receptive MHC-I complex, which is in turn contacted with the peptides of interest. In still other embodiments, the molecular chaperone (e.g., TAPBPR) is affixed to the solid substrate, and contacted with the molecular chaperone to form peptide receptive MHC-I complexes that include the chaperone. Such peptide receptive MHC-I complexes are then contacted with the peptides of interest.

In some embodiments, the peptide receptive MHC-I complex comprises a binding moiety, while the solid substrate comprises a capture moiety. The affixing the peptide-receptive unit to the solid substrate occurs through a reaction between the capture moiety and the binding moiety. In some such embodiments, a capture moiety in the plurality of capture moieties comprises streptavidin and the corresponding binding moiety comprises biotin. In some such embodiments, each MHC-I molecule in the one or more MHC-I molecules is tagged with an Avitag. The Avitag includes a single residue that can be biotinylated by a biotin ligase (such as BirA). As described herein, a binding moiety can be any part of a biomolecule or complex of biomolecules that specifically binds to a capture moiety. The binding moiety can be a naturally occurring structure on a biomolecule or one that is added via a chemical reaction (e.g., biotin or a protein tag). A capture moiety can be any composition that specifically binds to a binding moiety while the capture moiety is further bound to a solid substrate. In some embodiments, biotin conjugated to an MHC-I molecule or molecular chaperone is the binding moiety and streptavidin is bound to a solid substrate is the capture moiety. In other embodiments, streptavidin conjugated to an MHC-I molecule or molecular chaperone is the binding moiety and biotin bound to a solid substrate is the capture moiety.

B. Molecular Chaperones

As disclosed herein, molecular chaperones convert p*MHC-I to peptide receptive MHC-I complexes. Molecular chaperones can also create peptide receptive MHC-I complexes in mammalian cells which they are coexpressed with MHC-I constructs, including single chain MHC-I constructs (O'Rourke S M et al, Prot Eng Design Selection 32, 525-532 (2019); incorporated herein by reference in its entirety). In some embodiments, the molecular chaperone is Tapasin Binding Protein Related (TAPBPR).

TAPBPR includes a signal sequence, three extracellular domains comprising a unique membrane distal domain, an IgSF (immunoglobulin superfamily) V domain and an IgC1 domain, a transmembrane domain, and a cytoplasmic region. See, e.g., Boyle et al., *PNAS* 110 (9) 3465-3470 (2013), which is hereby incorporated herein by reference in its entirety. In some embodiments, the chaperone further includes one or more purification tags that facilitate the co-purification of the peptide-receptive unit/chaperone complex (e.g., an MHC-I/chaperone protein construct heterodimers). In some such embodiments, the chaperone comprises any tag that allows for co-purification of the peptide-receptive unit/chaperone complex. In some embodiments, the purification tag allows for affinity purification of the peptide-receptive unit/chaperone complexes from cell culture supernatant. Suitable purification tags that can be included in the chaperone protein construct include, but are not limited to, histidine tags, Strep-tags MYC-tags and HA-tags. In an exemplary embodiment, the purification tag is a Strep-tags®. TAPBPR can be made by any method known in the art, including those described in Morozov et al., Proc Natl Acad Sci 113, E1006-E1015 (2016) which is incorporated by reference herein, particularly for its teaching of methods of making TAPBPR chaperones.

In some embodiments, a stoichiometric amount of chaperone is used such that there is an excess of chaperone to p*MHC-I and so the p*MHC-I is more likely to form a complex with the chaperone. In such embodiments, the molar ratio of molecular chaperone to MHC-I molecules is 1:1 or more than 1:1, including more than 2:1, more than 3:1, more than 4:1, more than 5:1, more than 6:1, more than 7:1, more than 8:1, more than 9:1, or more than 10:1.

In other embodiments, a catalytic amount of chaperone is used such that there is an excess of p*MHC-I to chaperone and the chaperone converts the p*MHC-I to a peptide receptive MHC-I complex without forming a long-lasting complex. In such embodiments the molar ratio of molecular chaperone to MHC-I molecules is less than 1:1, less than 1:2, less than 1:3, less than 1:4, less than 1:5, less than 1:6, less than 1:7, less than 1:8, less than 1:9, or less than 1:10. In some such embodiments, the molar ratio of molecular chaperone to MHC-I molecules is less than 1:1, less than 1:2, less than 1:3, less than 1:4, less than 1:5, less than 1:6, less than 1:7, less than 1:8, less than 1:9, less than 1:10, less than 1:10, less than 1:100, less than 1:200, less than 1:300, less than 1:400, less than 1:500, less than 1:600, less than 1:700, less than 1:800, less than 1:900, less than 1:1,000, less than 1:5000, or less than In some embodiments, the peptide-receptive MHC-I complexes are highly stable and soluble. In some embodiments, the peptide-receptive unit/chaperone complexes can be stored at concentrations of up to 50, 100, 150, 200, 250, 300, 350, or 400 μM in solution without precipitation at 4° C. In certain embodiments, the peptide-receptive unit/chaperone complexes are completely soluble and remain peptide receptive in solution at a concentration of up to 400 μM at 4° C. for up to 1 month, 2 months, 3 months, 4 months, 5 months, 6 months, 7 months, 8 months, 9 months, 10 months, 11 months, or a year. The stability of MHC-I complexes (e.g., peptide deficient-MHC-I/chaperone complexes) can be measured, for example, using differential scanning fluorimetry techniques.

Creation of peptide receptive MHC-I complexes is described in, for example, WO2020/010261 (9 Jan. 2020) as well as Overall S et al, Nature Comm 11, 1909 (2020); both of which are incorporated by reference herein.

C. Peptides of Interest

As disclosed herein, peptides of interest can be loaded onto peptide receptive MHC-I complexes and then later analyzed. Peptides of interest can be introduced to peptide receptive MHC-I complexes at a molar excess of at least 2, 5, 10, 15, 20, 25, 30, 35, 40, 45, 50, 75 or 100 times to the peptide receptive MHC-I complex. In an exemplary embodiment, the peptide of interest is introduced at a molar excess of 50 times to the peptide receptive MHC-I complex and incubated at room temperature for at least 30 minutes, at least 1 hour, at least 2 hours, at least 5, hours, at least 10 hours, at least 15 hours, at least 18 hours, at least 24 hours, or more than 24 hours.

In some embodiments, a peptide of interest is 8-11 residues long. In some embodiments, the peptide of interest is a portion of a protein antigen, such as a tumor antigen, a viral or bacterial antigen, or an autoantigen (e.g. in the context of autoimmune diseases). Such peptides of interest, in combination with MHC-I, can be useful, for example, in the identification of T cells reactive to the antigen of interest in the context of a particular MHC-I allele.

Peptides of interest can be provided in a library, the library comprising a plurality of peptides of interest. The plurality of peptides in the library can all be of the same sequence or the plurality of peptides in the library can all have different sequences. The plurality of peptides in the library can all be derived from the same protein antigen or from multiple protein antigens all derived from the same tumor, bacterium, virus, or autoantigen.

In some embodiments, the library is obtained from a biological sample. A biological sample can be obtained from a subject for analysis using any of a variety of techniques including, but not limited to: collection of biological fluids (e.g., blood, urine, saliva, fecal matter, etc.) biopsy, surgery, and laser capture microscopy (LCM), and can include cells and/or other biological material (e.g. a pathogen) from the subject. In addition to the subjects described above, a biological sample can also be obtained from a prokaryote such as a bacterium, e.g., *Escherichia coli, Staphylococci* or *Mycoplasma pneumoniae*; an archae; a virus such as Hepatitis C virus, human immunodeficiency virus, SARS-CoV-2; or a viroid. A biological sample can also be obtained from a eukaryote, such as a patient derived organoid (PDO) or patient derived xenograft (PDX). Subjects from which biological samples can be obtained can be healthy or asymptomatic individuals, individuals that have or are suspected of having a disease (e.g., a patient with a disease such as cancer) or a pre-disposition to a disease, and/or individuals that are in need of therapy or suspected of needing therapy.

The biological sample can be obtained as a tissue sample, such as a tissue section, biopsy, a core biopsy, needle aspirate, or fine needle aspirate. The sample can be a fluid sample, such as a blood sample, urine sample, or saliva sample. The sample can be a skin sample, a colon sample, a cheek swab, a histology sample, a histopathology sample, a plasma or serum sample, a tumor sample, living cells, cultured cells, a clinical sample such as, for example, whole blood or blood-derived products, blood cells, or cultured tissues or cells, including cell suspensions.

The biological sample can be, for example, blood, plasma, serum, urine, saliva, mucosal excretions, sputum, stool, and tears. Biological samples can be derived from a homogeneous culture or population of the subjects or organisms mentioned herein or alternatively from a collection of several different organisms, for example, in a community or ecosystem.

Biological samples can include one or more diseased cells. A diseased cell can have altered metabolic properties, gene expression, protein expression, and/or morphologic features. Examples of diseases include inflammatory disorders, metabolic disorders, nervous system disorders, and cancer. Cancer cells can be derived from solid tumors, hematological malignancies, cell lines, or obtained as circulating tumor cells.

Examples of immune cells in a biological sample include, but are not limited to, B cells, T cells (e.g., cytotoxic T cells, natural killer T cells, regulatory T cells, and T helper cells), natural killer cells, cytokine induced killer (CIK) cells, myeloid cells, such as granulocytes (basophil granulocytes, eosinophil granulocytes, neutrophil granulocytes/hypersegmented neutrophils), monocytes/macrophages, mast cells, thrombocytes/megakaryocytes, and dendritic cells.

Peptide libraries can also be synthesized artificially. Peptide libraries (whether synthesized or derived from a biological sample) can comprise at least 10, at least 100, at least $10^3$, at least $10^4$, at least $10^5$, at least $10^6$, at least $10^7$, at least $10^8$, at least $10^9$, or at least $10^{10}$ different peptides of interest.

In some embodiments, purification of the pMHC resulting from contacting the peptides of interest with the peptide receptive MHC-I complex can be carried out using size exclusion chromatography (SEC). In some embodiments, the presence of the newly formed ligand/peptide-receptive unit complexes are confirmed using any technique known in the art, including, for example, liquid chromatography-mass spectrometry techniques.

D. pMHC-I

As described herein, peptides of interest with specificity for the MHC-I molecule in the peptide-receptive MHC-I complex can bind to the MHC-I molecule and form a peptide-MHC-I complex (pMHC-I) that includes an MHC class I heavy chain, β2 microglobulin and a peptide of interest. The pMHC-I does not include a molecular chaperone (such as TAPBPR) or a placeholder peptide. Preferably, 100%, of peptide-receptive MHC-I complexes are converted to pMHC-I, i.e. all MHC-I complexes in a plurality of MHC-I complexes include a peptide. In some embodiments, pMHC-I are combined to form pMHC-I multimers as described above.

In some embodiments, the pMHC-I is purified, thus separating the pMHC-I from any remaining free molecular chaperones, free peptides of interest, and/or free placeholder peptides, among other compounds. In some embodiments, the purification is achieved through gel filtration. In some embodiments, the purification comprises applying the ligand/peptide-receptive unit complex to a purification column. In some embodiments, the purification column is an immunoaffinity column. In some embodiments the one or more pMHC-I complexes comprise a poly-His tag (conjugated to the MHC class I heavy chain or β2 microglobulin) and the purification of the ligand/peptide-receptive unit complex comprises applying the ligand/peptide-receptive unit complex to a Ni-column.

E. Reagents and Kits

Also provided are reagents and kits thereof for practicing one or more of the above-described methods. The subject reagents and kits thereof may vary greatly. Reagents of interest include those mentioned above with respect to the methods of purifying peptides of interest described herein. Kits can include, for example, placeholder peptide MHC-I complexes (p*MHC-I), solid substrates, and/or molecular chaperones as disclosed herein. In some embodiments, the kits include MHC Class I heavy chains, β2 microglobulins, and placeholder peptides for making the p*MHC-Is described herein.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

EXAMPLES

Figure 4:
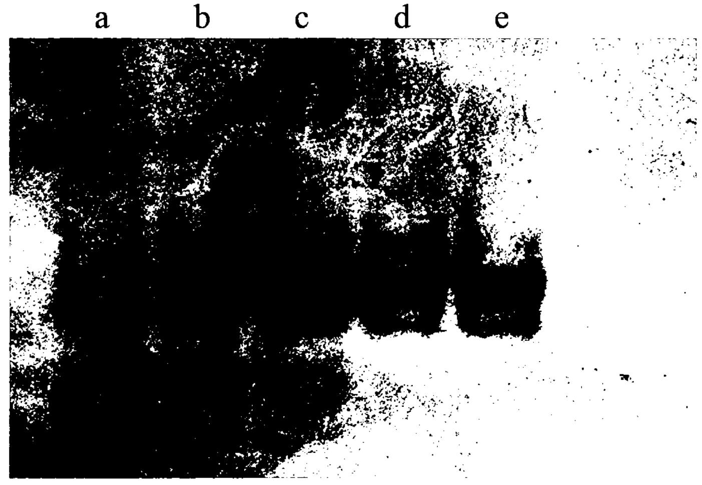
FIG. 4 illustrates results of a proof-of-concept assay where the HLA-A02-specific peptide ligand TAX releases HLA-A02 from the complex with biotinylated TAPBPR bound to Streptavidin-PE, in accordance with some embodiments.
Figures 5A, 5B:
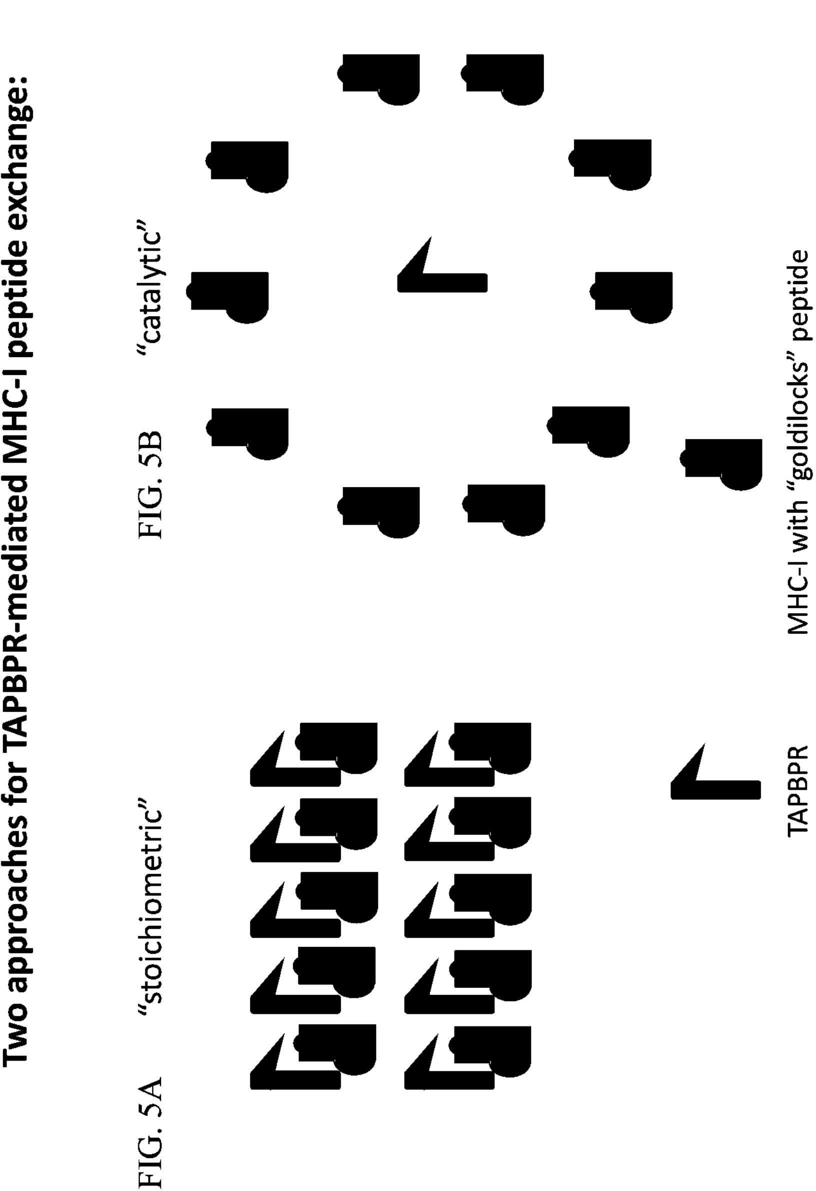
FIGS. 5A, 5B, and 5C provide schematics of alternative methods for enrichment of high-affinity peptides using TAPBPR-mediated MHC-I peptide exchange, in accordance with some embodiments.
Figure 5C:
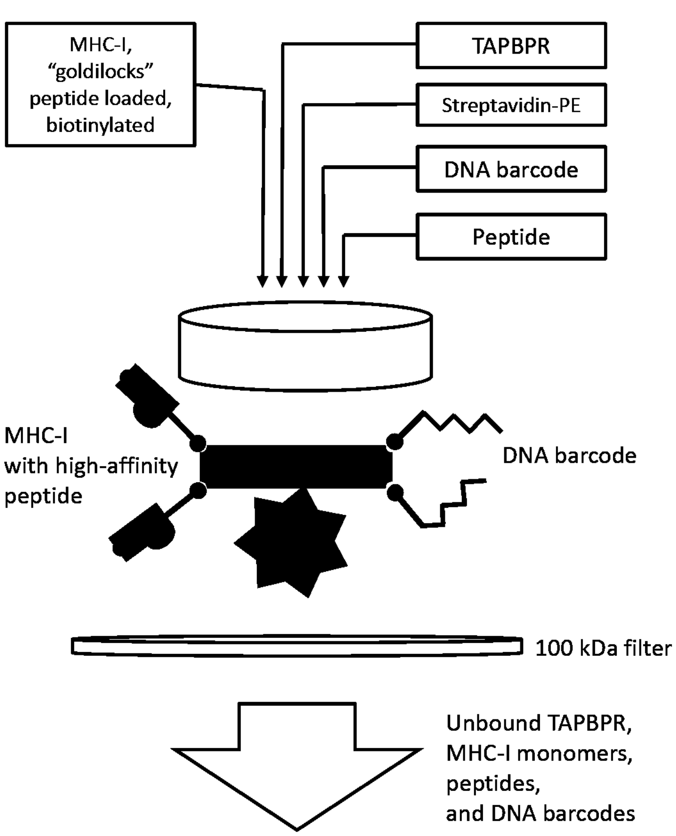

Example 1: Specific Peptide Ligand TAX Releases HLA-A2 from the Complex with Biotinylated TAPBPR Bound to Streptavidin-PE Recombinant TAPBPR conjugated to an AviTag was expressed and then biotinylated using BirA. Separately, the MHC-I molecule HLA-A02 was refolded with a placeholder (e.g., "goldilocks") peptide (e.g., G-TAX) to form a placeholder-peptide/MHC-I complex (p*MHC-I) which was purified as described in the Materials and Methods below. The biotinylated TAPBPR was mixed with the p*MHC-I to form peptide receptive MHC-I complexes. The peptide receptive MHC-I complexes were isolated by gel filtration and tetramerized with Streptavidin-PE. Referring now to FIG. 4, the peptide receptive MHC-I complexes were contacted with no peptide (lane a); 2500 pmol of the negative control P18-I10 peptide (lane b); 25 pmol of the HLA-A02 binding TAX peptide (lane c); 125 pmol TAX peptide (lane d); or 2500 pmol TAX peptide (lane e). FIG. 4 shows the results of analysis by native gel electrophoresis in 12% acrylamide gel.

Samples in which the tetramerized TAPBPR/HLA-A02 complexes were incubated with TAX peptide (e.g., specific for HLA-A02) exhibited a release of the HLA-A02 proteins from the TAPBPR/HLA-A02 complexes (e.g., samples c, d, and e). HLA-A02 proteins are visible on the protein native gel after staining (see Materials and Methods below). Conversely, samples in which the tetramerized TAPBPR/HLA-A02 complexes were incubated with control peptide (e.g., P18-I10 peptide non-specific for HLA-A02) or no peptide showed no HLA-A02 proteins (e.g., samples a and b).

Figure 6A:
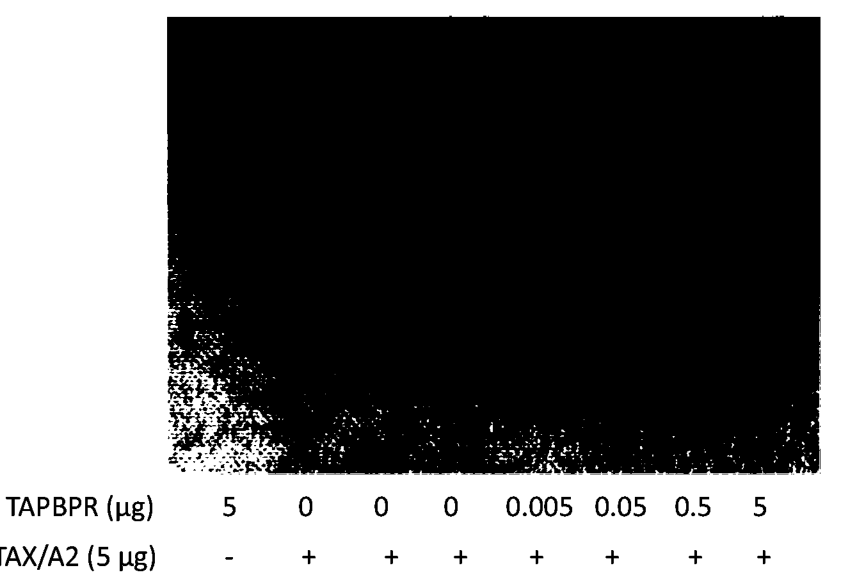
FIGS. 6A and 6B illustrate results of proof-of-concept assays for TAPBPR-mediated MHC-I peptide exchange, in accordance with some embodiments. TAPBPR catalyzes efficient peptide exchange when present at up to 1:1000 molar ratio with MHC-I.
Figure 6B:
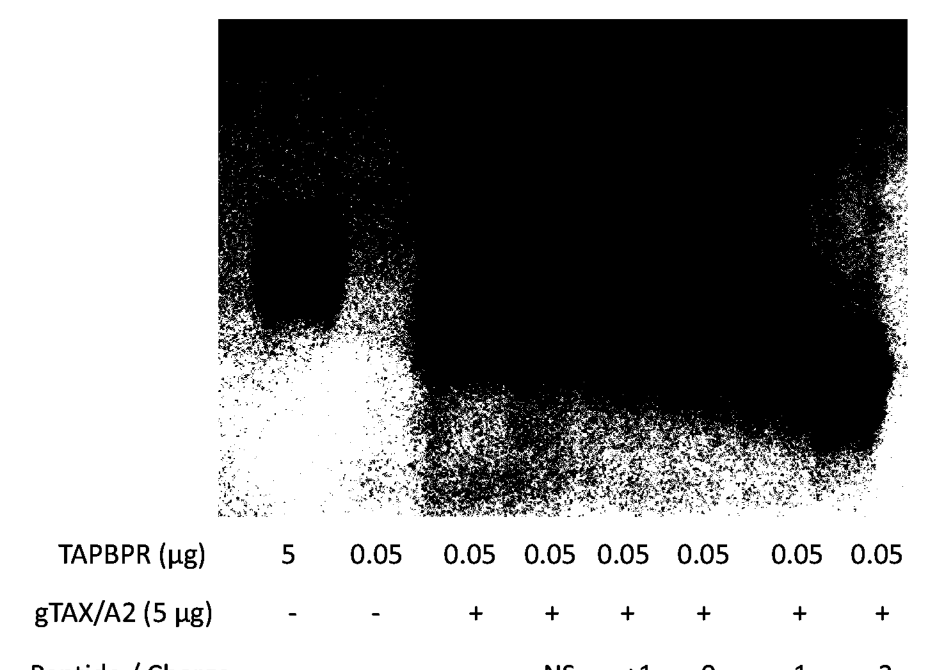

Example 2: TAPBPR Catalyzes Efficient Peptide Exchange Up to 1:1000 Molar Ratio with MHC-I A native gel electrophoresis assay was used to detect formation of pMHC species upon overnight incubation in the presence of an excess of peptide of interest and varying molar ratios of TAPBPR. FIG. 6A shows that under these conditions, complete peptide exchange on goldilocks/HLA-A*02:01 can be obtained using a TAPBPR:MHC molar ratio as low as 1:1000. No exchange is observed for a non-specific peptide, or in the absence of TAPBPR. FIG. 6B shows that the mobility of pMHC molecules is dependent on the net charge of the peptide, which allows the resolution of distinct protein bands of HLA-A*02:01 loaded with peptides of charges ranging from −2 to +1.

TAPBPR and HLA-A02 refolded with a placeholder goldilocks peptide ("gTAX/A2") were expressed as described in the Materials and Methods below. TAPBPR was incubated overnight at the indicated concentrations with 5 μg gTAX/A2 (the p*MHC-I) and a 10-fold molar excess of peptides specific for HLA-A02. Lanes with a—for peptide indicate that no high affinity peptide was added. Other high affinity peptides had a charge of −2. For samples containing 0.005 μg, 0.05 μg, 0.5 μg, and 5 μg TAPBPR, the resulting molar ratios of TAPBPR to MHC-I were 1:1000, 1:100, 1:10, and 1:1, respectively. Control incubations included TAPBPR alone, gTAX/A2 alone, gTAX/A2 incubated with a non-specific peptide ("NS"), and gTAX/A2 incubated with peptides specific for HLA-A02 but without TAPBPR. Reactions were analyzed using protein native gel electrophoresis in 12% acrylamide gel following incubation.

Figure 7A:
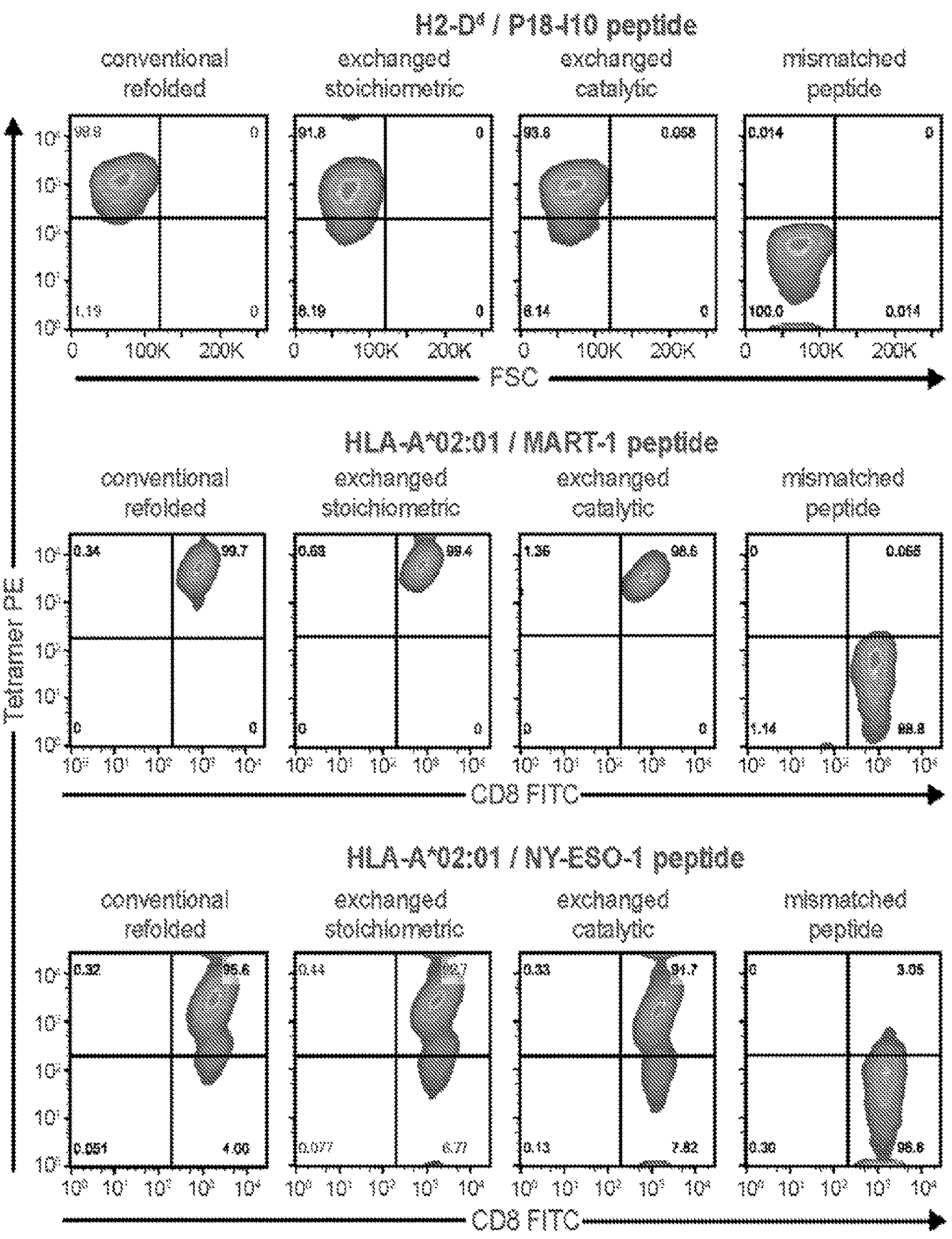

Example 3—MHC-I:Peptide Tetramers (pMHC-I) Made by the Disclosed Methods Perform Similarly to Commercially Available MHC-I:Peptide Tetramers Flow cytometry was performed using commercially available tetramers prepared by currently available methods ("conventional"), as well as by the disclosed methods involving TAPBPR peptide exchange using a stoichiometric amount of TAPBPR ("exchanged stoichiometric"), a catalytic amount of TAPBPR (1:100 TAPBPR: MHC-I) ("exchanged catalytic") or a mismatched peptide. FIGS. 7A and 7B show the results of representative flow cytometric analysis depicting murine cells expressing the B4.3.2 TCR (top row), DMF5 human T cells expressing the MART-1 TCR (middle row), and NY-ESO-1 human T cells expressing the NY-ESO-1 TCR (bottom row). Tetramers prepared by the disclosed methods performed similarly to tetramers commercially produced using conventional methods.

FIG. 7C illustrates a titration of P18410/H-2$D^d$ binding to B.4.2.3 cells (top), HLA-A*2:01/MART-1 binding to DMF5 cells (middle) and HLA-A*2:01/NY-ESO-1 peptide binding to NY-ESO-1 cells (bottom). The binding compares commercially available pMHC-I tetramers prepared using conventional methods (refolded) with pMHC-I tetramers prepared using the disclosed methods. The pMHC-I tetramers prepared by the disclosed methods here are prepared using the disclosed methods, in particular the method using a stoichiometric amount of TAPBPR ("exchanged") The percentage of cells staining positive with tetramer over a serial two-fold dilution series were plotted and EC50 values calculated by curve fitting to a sigmoidal 4PL, X is log (concentration) plot where $R^2$ values ranged between 0.97-0.99, using Graph Pad Prism version 8 for Mac (GraphPad Software, La Jolla, California USA). Data shown is representative of triplicate assays and error-bars are standard deviation from the mean.

Example 4—Production of pMHC by TAPBPR Exchange is Higher than Conventional Methods Using the TAX/HLA-A*02:01 system as a benchmark, it was also determined that the overall yield of pMHC molecules prepared by TAPBPR exchange is approximately 2.5 times higher relative to the use of a photo-cleavable ligand (see, e.g., Bakket et al., Proc. Natl. Acad. Sci. U.S.A., 105:3825-3830 (2008)) and approximately 10 times higher relative to the use of an empty HLA-A*02:01 molecule with an engineered disulfide bond (see, e.g., Saini et al., *Sci Immunol* 4, oi:10.1126/sciimmunol.aau9039 (2019)).

Figure 1:
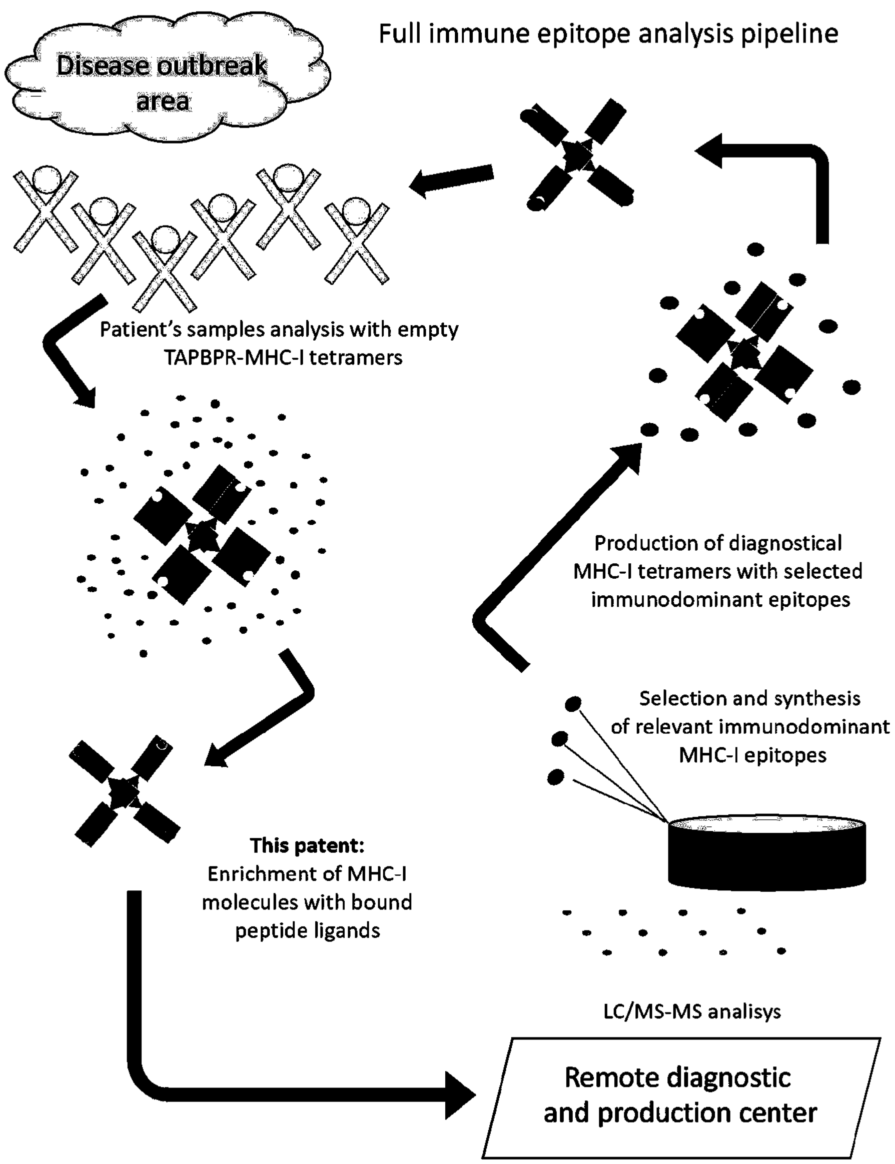
FIG. 1 provides a schematic of an immune epitope analysis pipeline, in accordance with some embodiments of representative clinical applications.

Example 5—Use of Peptide Receptive MHC-I Produced by TAPBPR to Identify Antigenic Peptides Referring to FIG. 1, the disclosed systems and methods can be used in a pipeline for rapid identification and/or analysis of high-affinity MHC-I antigenic peptides from a wide range of clinical samples. For example, some embodiments described in FIGS. 2 and 3 make use of column-packed TAPBPR/MHC-I complexes that can be used as kit sets in field areas and/or hospitals without relying on sophisticated facilities for express analysis and primary MHC-I epitope collection. Such areas can include disease outbreak zones, remote study sites, or areas undergoing vaccine and/or drug trials.

In some embodiments of the pipeline illustrated in FIG. 1, patient samples are collected at field sites and applied to columns comprising peptide receptive MHC-I complexes produced using TAPBPR. MHC-I molecules enriched with bound peptide ligands can be purified for further analysis. For example, the MHC-I molecules enriched with bound peptide ligands can be sent to centralized clinical and/or research centers for MHC-I epitope identification (e.g., by using LC/MS/MS, cross-referencing with epitope databases, and/or machine learning techniques to predict the specificities of the enriched peptide ligands for various MHC-I alleles). Collected patient samples can also be sent to centralized clinical and/or research centers.

Relevant MHC-I binding peptides identified using the disclosed methods can then be used to produce diagnostic pMHC-I tetramers that include the relevant MHC-I binding peptide, as described in See, e.g., Overall et al., "High Throughput pMHC-I Tetramer Library Production Using Chaperone Mediated Peptide Exchange," bioRxiv, doi: 10.1101/653477 (2019), which is hereby incorporated by reference herein in its entirety.

Example 6—Placeholder Peptide-MHC Monomer and Recombinant TAPBPR Expression and Purification Plasmid DNA encoding the luminal domain of class I MHC (MHC-I) heavy chains H2-$D^d$, HLA-A*02:01, and light chain $\beta_2$-microglobulin (h$\beta_2$m,) were provided by the NIH Tetramer Core Facility (Emory University), and transformed into *Escherichia coli* BL21(DE3) (Novagen). MHC-I proteins were expressed in Luria-Broth media, and inclusion bodies (IBs) were purified as described in Garboczi et al., *PNAS* 89(8) 3429-3433 (1992). For in vitro refolding of pMHC-I molecules, 10 mg of synthetic peptides (derived from either the HIV gp160 epitope P18-I10: RGPGRAFVTI for H2-$D^d$, or the HTLV-1 epitope $TAX_{11-19}$: LLFGYPVYV and the Analog Melan-A/MART-$1_{26-35}$ (A27L) epitope: ELAGIGILTV for HLA-A*02:01) and a 200 mg mixture of heavy chain:light chain IBs at a 1:3 molar ratio were slowly diluted over 24 hours into refolding buffer (0.4 M Arginine-HCl, 2 mM EDTA, reduced/oxidized L-glutathione 4.9/0.57 mM, 100 mM Tris pH 8.0) at 4° C., while stirring. To obtain suitable pMHC-I molecules for TAPBPR-mediated peptide exchange, we used N-terminally truncated, "placeholder" versions of the P18-I10 or TAX peptides (_GPGRAFVTI and _LFGYPVYV, respectively). The resulting placeholder peptide/MHC-I complexes are referred to as p*MHC-I herein. For each peptide/MHC I combination, refolding proceeded for four days at 4° C., without stirring. Purification of all pMHC-I complexes was performed by size exclusion chromatography (SEC) using a HiLoad 16/600 Superdex 75 column (150 mM NaCl, 25 mM Tris pH 8), followed by anion exchange chromatography on a mono Q 5/50 GL column at 1 mL/min using a 40 minute 0-100% gradient of buffer A (50 mM NaCl, 25 mM Tris pH 8) and buffer B (1M NaCl, 25 mM Tris pH 8). The luminal domain of TAPBPR was expressed using a stable Drosophila S2 cell line (Morozov et al, Proc Natl Acad Sci 113, E1006-E1015 (2016); incorporated by reference herein), and purified in a similar manner to the pMHC-I molecules. All proteins were exhaustively buffer-exchanged into 20 mM $NaH_2PO_4$, pH 7.2, 100 mM NaCl. The presence of the disclosed bound peptides was validated by LC/MS on an LTQ-Orbitrap Velos Pro MS instrument. Typical protein yields from a 1 L expression were in the range from 5 to 10 mg, after purification.

Example 7—Immunoblot

Proteins (from cell supernatant and cytoplasmic lysate) were electrophorized on 12% SDS gels in MOPS gel running buffer (Thermo Scientific, Waltham, MA). For Immunoblot, proteins were electrophoresed, transferred to a PDVF membrane, then probed with a polyclonal rabbit anti-TAPBPR antibody or a murine anti-B2M followed by an affinity purified secondary HRP conjugated anti-species antibody (Jackson ImmunoResearch, West Grove, PA) and visualized using an Innotech FluoChem2 system (Genetic Technologies Grover, MO).

Example 8—Peptide Receptive MHC-I Complex Purification

Culture media was harvested and pre-cleared by centrifugation at 250 g for 10 minutes. The media was adjusted to contain 25 mM Tris pH 8, 1 mM EDTA and 27 mg/L of avidin and filtered (0.22 micron) before affinity purification on a StrepTrap HP affinity column (GE Healthcare, Chicago IL). Bound biotinylated protein was washed with 10 column volumes of wash buffer (25 mM Tris pH 8, 100 mM NaCl, 1 mM EDTA) and eluted with 2.5 mM desthiobiotin/wash buffer. The complex was concentrated from approximately 6 mL to 0.5 mL on a 30 kD cutoff MicrosepAdvance filter (Pall, New York, NY), and digested overnight with TEV (Tobacco Etch Protein) in TEV cleavage buffer (25 mM Tris pH 8, 100 mM NaCl 1 mM EDTA, 3 mM/0.3 M glutathione redox buffer at 4° C. Complex was recovered by gel filtration (SEC) on a Superdex 200 10/300 increase column (GE Healthcare, Chicago, IL) at a flow rate of 0.5 mL/min in 50 mM Tris pH 7.5 buffer containing 100 mM NaCl at room temperature. MHC-I/TAPBPR complexes eluted at 26.5-27 minutes GM did peptide was (10 mM) was added to the running buffer during chromatography.

Example 8—Native Gel Shift Assay of Peptide Binding to Peptide Receptive Complex MHC-I/TAPBPR complexes were incubated with the indicated molar ratio of relevant (TAX or MART 1) or irrelevant (P18-I10 or NIH) peptide for 1 h at room temperature at pH 7.5 in Tris buffer with 50 mM NaCl. Samples were electrophoresed at 90 V on a 12% polyacrylamide gel in 25 mM T IS pH 8.8, 192 mM glycine, at 4° C. for 4.0 hours and developed using InstantBlue (Expedeon San Diego, CA).

Example 9—Tetramer Formation

Tetramer formation The procedure for production of peptide loaded tetramers using TAPBPR mediated exchange is described in See, e.g., Overall et al., "High Throughput pMHC-I Tetramer Library Production Using Chaperone Mediated Peptide Exchange," bioRxiv, doi:10.1101/653477 (2019), which is hereby incorporated by reference in its entirety herein. Briefly, SEC purified (unzipped) MHC-I/TAPBPR complex molecules were biotinylated via an AVI-TAG (GLNDIFEAQKIEWHE) on the MHC-I molecule using biotin ligase (BirA) (Avidity.com Co), according to the manufacturer's instructions. Biotinylated MHC-I/TAPBPR complex was buffer exchanged into PBS pH 7.4 using a PD-10 desalting column. Biotinylation was confirmed by SDS-PAGE in the presence of excess streptavidin. Tetramerization of peptide receptive MHC-I was performed by adding a 2:1 molar ratio of biotinylated MHC-I/TAPBPR to streptavidin-PE or streptavidin-APC (Prozyme Hayward, CA) in five additions over 1 h on ice. Peptide-deficient MHC-I/TAPBPR tetramers were then exchanged with peptides of interest by adding a 20-molar excess of peptide to each well and incubating for 1 hour. A solution of 8M biotin (to block any free streptavidin sites) was added and incubated for a further 1 h at room temperature. After exchange, tetramers were transferred to 100 kDa spin columns (Amicon, Millipore, Burlington, Ma) and washed with 1000 volumes of PBS to remove TAPBPR and excess peptide. After washing, exchanged tetramers were pooled and stored at 4° C. for up to 3 weeks.

All cited references are herein expressly incorporated by reference in their entirety.

Whereas particular embodiments of the invention have been described above for purposes of illustration, it will be appreciated by those skilled in the art that numerous variations of the details may be made without departing from the invention as described in the appended claims.

Sequences:

β-2 microglobulin
IQRTPKIQVYSRHPAENGKSNFLNCYVSGFHPSDIEVDLLKNGERIEKV
EHSDLSFSKDWSFYLLYYTEFTPTEKDEYACRVNHVTLSQPKIVKWDRD
M (SEQ ID NO: 1)

HLA-A*02:01
GSHSMRYFFTSVSRPGRGEPRFIAVGYVDDTQFVRFDSDAASQRMEPRA
PWIEQEGPEYWDGETRKVKAHSQTHRVDLGTLRGYYNQSEAGSHTVQRM
YGCDVGSDWRFLRGYHQYAYDGKDYIALKEDLRSWTAADMAAQTTKHKW
EAAHVAEQLRAYLEGTCVEWLRRYLENGKETLQRTDAPKTHMTHHAVSD

-continued

| Sequences: |
|---|
| HEATLRCWALSFYPAEITLTWQRDGEDQTQDTELVETRPAGDGTFQKWA AVVVPSGQEQRYTCHVQHEGLPKPLTLRWEPS (SEQ ID NO: 2) |
| HLA-A*24:02 GSSHSMRYFSTSVSRPGRGEPRFIAVGYVDDTQFVRFDSDAASQRMEPR APWIEQEGPEYWDEETGKVKAHSQTDRENLRIALRYYNQSEAGSHTLQM MFGCDVGSDGRFLRGYHQYAYDGKDYIALKEDLRSWTAADMAAQITKRK WEAAHVAEQQRAYLEGTCVDGLRRYLENGKETLQRTDPPKTHMTHHPIS DHEATLRCWALGFYPAEITLTWQRDGEDQTQDTELVETRPAGDGTFQKW AAVVVPSGEEQRYTCHVQHEGLPKPLTLRWEPS (SEQ ID NO: 3) |

-continued

| Sequences: |
|---|
| HLA-A*68:02 GSHSMRYFYTSMSRPGRGEPRFIAVGYVDDTQFVRFDSDAASQRMEPRA PWIEQEGPEYWDRNTRNVKAQSQTDRVDLGTLRGYYNQSEAGSHTIQRM YGCDVGPDGRFLRGYHQYAYDGKDYIALKEDLRSWTAADMAAQTTKHKW EAAHVAEQWRAYLEGTCVEWLRRYLENGKETLQRTDAPKTHMTHHAVSD HEATLRCWALSFYPAEITLTWQRDGEDQTQDTELVETRPAGDGTFQKWV AVVVPSGQEQRYTCHVQHEGLPKPLTLKWEPS (SEQ ID NO: 4) |

What is claimed is:

1. A method of purifying a peptide of interest that binds an MHC class I molecule, the method comprising:

contacting a precursor peptide-MHC-I complex (p*MHC-I) comprising a MHC Class I heavy chain, a β2 microglobulin, and a precursor peptide with a molecular chaperone, thereby forming a peptide receptive MHC-I complex comprising the MHC class I heavy chain and the β2 microglobulin;

affixing the peptide receptive MHC-I complex to a solid substrate;

contacting the peptide receptive MHC-I complex with a plurality of peptides of interest, wherein at least one of the plurality of peptides of interest binds the peptide-receptive MHC-I complex, resulting in the formation of a peptide-MHC-I complex (pMHC-I); and removing the pMHC-I from the solid substrate, thereby purifying the peptide of interest.

2. The method of claim 1 further comprising eluting the peptide of interest from the MHC-Class I molecule.

3. The method of claim 2, wherein the eluting comprises contacting the pMHC-I with a solution of acidic pH.

4. The method of claim 3, wherein the solution is a solution of 10% acetic acid.

5. The method of claim 1, further comprising identifying the peptide of interest.

6. The method of claim 5, wherein the peptide of interest is identified by a mass spectrometry technique.

7. The method of claim 6, wherein the mass spectrometry technique is liquid chromatography-mass spectrometry (LC-MS) or liquid chromatography-tandem mass spectrometry (LC-MS-MS).

8. The method of claim 1, wherein the peptide receptive MHC-I complex is affixed to the solid substrate via an interaction between the MHC class I heavy chain or the β2 microglobulin and the solid substrate.

9. The method of claim 8, wherein the MHC Class I heavy chain or the β2 microglobulin is biotinylated and the solid substrate comprises a biotin binding protein.

10. The method of any of claim 1, wherein the peptide receptive MHC-I complex comprises a placeholder peptide.

11. The method of claim 1, wherein the molecular chaperone is at a molar excess relative to the p*MHC-I.

12. The method of claim 11, wherein the molecular chaperone is at a ratio of more than 1:1, more than 2:1, more than 3:1, more than 4:1, more than 5:1, more than 6:1, more than 7:1, more than 8:1, more than 9:1, or more than 10:1 relative to the p*MHC-I.

13. The method of claim 1, wherein the p*MHC-I is at a molar excess relative to the molecular chaperone.

14. The method of claim 1, wherein the molecular chaperone is at a ratio of less than 1:1, less than 1:2, less than 1:5, less than 1:10, less than 1:50, less than 1:100, less than 1:500, or less than 1:1000 relative to the p*MHC-I.

15. The method of any of claim 1, wherein the solid substrate comprises a bead.

16. The method of 15, wherein the bead comprises a molecular barcode.

17. The method of claim 15, wherein the bead is formed into a column.

18. The method of any of claim 1, wherein the molecular chaperone is Tapasin Binding Protein Related (TAPBPR).

19. The method of any of claim 1, wherein the MHC class I heavy chains are selected from human HLA-A, human HLA-B, human HLA-C, mouse H-2D, or mouse H-2L.

20. The method of claim 1, wherein the MHC class I heavy chain is selected from HLA-A: 02, HLA-A: 24, or HLA-A: 68.

* * * * *

SEQUENCE LISTING

```
<160> NUMBER OF SEQ ID NOS: 4

<210> SEQ ID NO 1
<211> LENGTH: 99
<212> TYPE: PRT
<213> ORGANISM: Artificial Sequence
<220> FEATURE:
<223> OTHER INFORMATION: Synthetic protein (beta-2 microglobulin)

<400> SEQUENCE: 1

Ile Gln Arg Thr Pro Lys Ile Gln Val Tyr Ser Arg His Pro Ala Glu
1               5                   10                  15

Asn Gly Lys Ser Asn Phe Leu Asn Cys Tyr Val Ser Gly Phe His Pro
            20                  25                  30

Ser Asp Ile Glu Val Asp Leu Leu Lys Asn Gly Glu Arg Ile Glu Lys
        35                  40                  45

Val Glu His Ser Asp Leu Ser Phe Ser Lys Asp Trp Ser Phe Tyr Leu
    50                  55                  60

Leu Tyr Tyr Thr Glu Phe Thr Pro Thr Glu Lys Asp Glu Tyr Ala Cys
65                  70                  75                  80

Arg Val Asn His Val Thr Leu Ser Gln Pro Lys Ile Val Lys Trp Asp
                85                  90                  95

Arg Asp Met


<210> SEQ ID NO 2
<211> LENGTH: 277
<212> TYPE: PRT
<213> ORGANISM: Artificial Sequence
<220> FEATURE:
<223> OTHER INFORMATION: Synthetic protein (HLA-A*02:01)

<400> SEQUENCE: 2

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr His Arg Val Asp Leu Gly Thr
65                  70                  75                  80

Leu Arg Gly Tyr Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110
```

```
Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Thr Thr Lys
    130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Pro Ser
        275


<210> SEQ ID NO 3
<211> LENGTH: 278
<212> TYPE: PRT
<213> ORGANISM: Artificial Sequence
<220> FEATURE:
<223> OTHER INFORMATION: Synthetic protein (HLA-A*24:02)

<400> SEQUENCE: 3

Gly Ser Ser His Ser Met Arg Tyr Phe Ser Thr Ser Val Ser Arg Pro
1               5                   10                  15

Gly Arg Gly Glu Pro Arg Phe Ile Ala Val Gly Tyr Val Asp Asp Thr
            20                  25                  30

Gln Phe Val Arg Phe Asp Ser Asp Ala Ala Ser Gln Arg Met Glu Pro
        35                  40                  45

Arg Ala Pro Trp Ile Glu Gln Glu Gly Pro Glu Tyr Trp Asp Glu Glu
    50                  55                  60

Thr Gly Lys Val Lys Ala His Ser Gln Thr Asp Arg Glu Asn Leu Arg
65                  70                  75                  80

Ile Ala Leu Arg Tyr Tyr Asn Gln Ser Glu Ala Gly Ser His Thr Leu
                85                  90                  95

Gln Met Met Phe Gly Cys Asp Val Gly Ser Asp Gly Arg Phe Leu Arg
            100                 105                 110

Gly Tyr His Gln Tyr Ala Tyr Asp Gly Lys Asp Tyr Ile Ala Leu Lys
        115                 120                 125

Glu Asp Leu Arg Ser Trp Thr Ala Ala Asp Met Ala Ala Gln Ile Thr
    130                 135                 140

Lys Arg Lys Trp Glu Ala Ala His Val Ala Glu Gln Gln Arg Ala Tyr
145                 150                 155                 160

Leu Glu Gly Thr Cys Val Asp Gly Leu Arg Arg Tyr Leu Glu Asn Gly
                165                 170                 175

Lys Glu Thr Leu Gln Arg Thr Asp Pro Pro Lys Thr His Met Thr His
            180                 185                 190
```

```
His Pro Ile Ser Asp His Glu Ala Thr Leu Arg Cys Trp Ala Leu Gly
        195                 200                 205

Phe Tyr Pro Ala Glu Ile Thr Leu Thr Trp Gln Arg Asp Gly Glu Asp
    210                 215                 220

Gln Thr Gln Asp Thr Glu Leu Val Glu Thr Arg Pro Ala Gly Asp Gly
225                 230                 235                 240

Thr Phe Gln Lys Trp Ala Ala Val Val Val Pro Ser Gly Glu Glu Gln
                245                 250                 255

Arg Tyr Thr Cys His Val Gln His Glu Gly Leu Pro Lys Pro Leu Thr
            260                 265                 270

Leu Arg Trp Glu Pro Ser
        275


<210> SEQ ID NO 4
<211> LENGTH: 277
<212> TYPE: PRT
<213> ORGANISM: Artificial Sequence
<220> FEATURE:
<223> OTHER INFORMATION: Synthetic protein (HLA-A*68:02)

<400> SEQUENCE: 4

Gly Ser His Ser Met Arg Tyr Phe Tyr Thr Ser Met Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Arg Asn Thr
    50                  55                  60

Arg Asn Val Lys Ala Gln Ser Gln Thr Asp Arg Val Asp Leu Gly Thr
65                  70                  75                  80

Leu Arg Gly Tyr Tyr Asn Gln Ser Glu Ala Gly Ser His Thr Ile Gln
                85                  90                  95

Arg Met Tyr Gly Cys Asp Val Gly Pro Asp Gly Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Thr Thr Lys
    130                 135                 140

His Lys Trp Glu Ala Ala His Val Ala Glu Gln Trp Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240
```

-continued

```
Phe Gln Lys Trp Val Ala Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Lys Trp Glu Pro Ser
        275
```